United States Patent
Goldshleger et al.

(10) Patent No.: US 9,492,322 B2
(45) Date of Patent: Nov. 15, 2016

(54) IMAGING SURGICAL TARGET TISSUE BY NONLINEAR SCANNING

(75) Inventors: Ilya Goldshleger, Irvine, CA (US);
Guy Holland, San Clemente, CA (US);
Ferenc Raksi, Mission Viejo, CA (US)

(73) Assignee: ALCON LENSX, INC., Aliso Viejo, CA (US)

( * ) Notice: Subject to any disclaimer, the term of this patent is extended or adjusted under 35 U.S.C. 154(b) by 638 days.

(21) Appl. No.: 12/619,606

(22) Filed: Nov. 16, 2009

(65) Prior Publication Data

US 2011/0118609 A1    May 19, 2011

(51) Int. Cl.
*A61B 6/00* (2006.01)
*A61F 9/008* (2006.01)
*A61B 5/00* (2006.01)

(52) U.S. Cl.
CPC .......... *A61F 9/008* (2013.01); *A61F 9/00825* (2013.01); *A61B 5/0073* (2013.01); *A61F 9/00829* (2013.01); *A61F 2009/0087* (2013.01); *A61F 2009/0088* (2013.01); *A61F 2009/00851* (2013.01); *A61F 2009/00882* (2013.01)

(58) Field of Classification Search
CPC .......... A61F 2009/00851; A61F 2009/00882; A61F 9/008; A61F 2009/0087–2009/00876; A61F 9/00825–9/00829; A61B 5/0073
USPC ......... 345/418; 351/205, 206, 208; 356/479, 356/497; 382/199, 268; 600/476; 606/4, 5
See application file for complete search history.

(56) References Cited

U.S. PATENT DOCUMENTS

| | | | |
|---|---|---|---|
| 4,164,222 A | 8/1979 | Prokhorov et al. | |
| 4,198,143 A | 4/1980 | Karasawa | |
| 4,235,529 A | 11/1980 | Kawase et al. | |
| 4,465,348 A | 8/1984 | Lang | |
| 4,520,816 A | 6/1985 | Schachar et al. | |
| 4,533,222 A | 8/1985 | Ishikawa | |
| 4,538,608 A | 9/1985 | L'Esperance, Jr. | |
| 4,554,917 A | 11/1985 | Tagnon | |
| 4,638,801 A | 1/1987 | Daly et al. | |

(Continued)

FOREIGN PATENT DOCUMENTS

| EP | 1444946 A1 | 8/2004 |
|---|---|---|
| EP | 2322083 A1 | 5/2011 |

(Continued)

OTHER PUBLICATIONS

Kim, Tae Hoon, Authorized Officer, Korean Intellectual Property Office, PCT International Application No. PCT/US2011/025332, in International Search Report, mailed Sep. 16, 2011, 8 pages.

(Continued)

*Primary Examiner* — Serkan Akar
(74) *Attorney, Agent, or Firm* — S. Brannon Latimer

(57) ABSTRACT

Systems and techniques for laser surgery based on imaging a target tissue by nonlinear scanning are presented. In one implementation, a method for guiding an eye surgery can include the steps of: positioning an eye in relation to an imaging system; creating first scan data by determining a depth of an eye target region at a first set of points along a first arc; creating second scan data by determining a depth of the eye target region at a second set of points along a second arc; determining target region parameters based on the first and second scan data; and adjusting one or more surgical position parameters according to the determined target region parameters.

20 Claims, 25 Drawing Sheets

(56) References Cited

U.S. PATENT DOCUMENTS

| | | |
|---|---|---|
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,112,328 A | 5/1992 | Taboada et al. |
| 5,139,022 A | 8/1992 | Lempert |
| 5,246,435 A | 9/1993 | Bille et al. |
| 5,255,025 A | 10/1993 | Volk |
| 5,286,964 A | 2/1994 | Fountain |
| 5,321,501 A | 6/1994 | Swanson et al. |
| 5,336,215 A | 8/1994 | Hsueh et al. |
| 5,391,165 A | 2/1995 | Fountain et al. |
| 5,439,462 A | 8/1995 | Bille et al. |
| 5,491,524 A | 2/1996 | Hellmuth et al. |
| 5,493,109 A | 2/1996 | Wei et al. |
| 5,549,632 A | 8/1996 | Lai |
| 5,656,186 A | 8/1997 | Mourou et al. |
| 5,738,676 A | 4/1998 | Hammer et al. |
| 5,779,696 A | 7/1998 | Berry et al. |
| 5,795,295 A | 8/1998 | Hellmuth et al. |
| 5,936,706 A | 8/1999 | Takagi |
| 5,954,648 A | 9/1999 | Van Der Brug |
| 5,954,711 A | 9/1999 | Ozaki et al. |
| 5,994,690 A | 11/1999 | Kulkarni et al. |
| 6,004,314 A | 12/1999 | Wei et al. |
| 6,095,648 A | 8/2000 | Birngruber et al. |
| 6,099,522 A | 8/2000 | Knopp et al. |
| 6,137,585 A | 10/2000 | Hitzenberger et al. |
| 6,254,595 B1 | 7/2001 | Juhasz et al. |
| 6,288,784 B1 | 9/2001 | Hitzenberger et al. |
| 6,314,311 B1 | 11/2001 | Williams et al. |
| 6,317,616 B1 | 11/2001 | Glossop |
| 6,337,925 B1 * | 1/2002 | Cohen et al. ............... 382/199 |
| 6,377,349 B1 | 4/2002 | Fercher |
| 6,379,005 B1 | 4/2002 | Williams et al. |
| 6,451,009 B1 | 9/2002 | Dasilva et al. |
| 6,454,761 B1 | 9/2002 | Freedman |
| 6,497,701 B2 | 12/2002 | Shimmick et al. |
| 6,529,758 B2 | 3/2003 | Shahidi |
| 6,579,282 B2 | 6/2003 | Bille et al. |
| 6,623,476 B2 | 9/2003 | Juhasz et al. |
| 6,687,010 B1 | 2/2004 | Horii et al. |
| 6,730,074 B2 | 5/2004 | Bille et al. |
| 6,741,359 B2 | 5/2004 | Wei et al. |
| 6,751,033 B2 | 6/2004 | Goldstein et al. |
| 6,755,819 B1 | 6/2004 | Waelti |
| 6,763,259 B1 | 7/2004 | Hauger et al. |
| 6,769,769 B2 | 8/2004 | Podoleanu et al. |
| 6,775,007 B2 | 8/2004 | Izatt et al. |
| 6,863,667 B2 | 3/2005 | Webb et al. |
| 6,887,232 B2 | 5/2005 | Bille |
| 6,899,707 B2 | 5/2005 | Scholler et al. |
| 6,932,807 B1 | 8/2005 | Tomita et al. |
| 6,991,629 B1 | 1/2006 | Juhasz et al. |
| 6,996,905 B2 | 2/2006 | Meguro |
| 7,006,232 B2 | 2/2006 | Rollins et al. |
| 7,018,376 B2 | 3/2006 | Webb et al. |
| 7,027,233 B2 | 4/2006 | Goldstein et al. |
| 7,061,622 B2 | 6/2006 | Rollins et al. |
| 7,072,045 B2 | 7/2006 | Chen et al. |
| 7,072,047 B2 | 7/2006 | Westphal et al. |
| 7,079,254 B2 | 7/2006 | Kane et al. |
| 7,102,756 B2 | 9/2006 | Izatt et al. |
| 7,113,818 B2 | 9/2006 | Podoleanu et al. |
| 7,126,693 B2 | 10/2006 | Everett et al. |
| 7,130,054 B2 | 10/2006 | Ostrovsky et al. |
| 7,133,137 B2 | 11/2006 | Shimmick |
| 7,139,077 B2 | 11/2006 | Podoleanu et al. |
| 7,145,661 B2 | 12/2006 | Hitzenberger |
| 7,148,970 B2 | 12/2006 | de Boer |
| 7,184,148 B2 | 2/2007 | Alphonse |
| 7,207,983 B2 | 4/2007 | Hahn et al. |
| 7,248,371 B2 | 7/2007 | Chan et al. |
| 7,268,885 B2 | 9/2007 | Chan et al. |
| 7,280,221 B2 | 10/2007 | Wei |
| 7,307,733 B2 | 12/2007 | Chan et al. |
| 7,310,150 B2 | 12/2007 | Guillermo et al. |
| 7,312,876 B2 | 12/2007 | Chan et al. |
| 7,319,566 B2 | 1/2008 | Prince et al. |
| 7,329,002 B2 | 2/2008 | Nakanishi |
| 7,330,270 B2 | 2/2008 | O'Hara et al. |
| 7,330,273 B2 | 2/2008 | Podoleanu et al. |
| 7,335,223 B2 | 2/2008 | Obrebski |
| 7,336,366 B2 | 2/2008 | Choma et al. |
| 7,342,659 B2 | 3/2008 | Horn et al. |
| 7,347,548 B2 | 3/2008 | Huang et al. |
| 7,352,444 B1 | 4/2008 | Seams et al. |
| 7,355,716 B2 | 4/2008 | de Boer et al. |
| 7,364,296 B2 | 4/2008 | Miller et al. |
| 7,365,856 B2 | 4/2008 | Everett et al. |
| 7,365,859 B2 | 4/2008 | Yun et al. |
| 7,370,966 B2 | 5/2008 | Fukuma et al. |
| 7,371,230 B2 | 5/2008 | Webb et al. |
| 7,372,578 B2 | 5/2008 | Akiba et al. |
| 7,388,672 B2 | 6/2008 | Zhou et al. |
| 7,390,089 B2 | 6/2008 | Loesel et al. |
| 7,400,410 B2 | 7/2008 | Baker et al. |
| 7,402,159 B2 | 7/2008 | Loesel et al. |
| 7,416,300 B2 | 8/2008 | Wei et al. |
| 7,426,037 B2 | 9/2008 | Ostrovsky et al. |
| 7,433,046 B2 | 10/2008 | Everett et al. |
| 7,452,077 B2 | 11/2008 | Meyer et al. |
| 7,452,080 B2 | 11/2008 | Wiltberger et al. |
| 7,461,658 B2 | 12/2008 | Jones et al. |
| 7,466,423 B2 | 12/2008 | Podoleanu et al. |
| 7,470,025 B2 | 12/2008 | Iwanaga |
| 7,477,764 B2 | 1/2009 | Haisch |
| 7,480,058 B2 | 1/2009 | Zhao et al. |
| 7,480,059 B2 | 1/2009 | Zhou et al. |
| 7,488,070 B2 | 2/2009 | Hauger et al. |
| 7,488,930 B2 | 2/2009 | Ajgaonkar et al. |
| 7,492,466 B2 | 2/2009 | Chan et al. |
| 7,503,916 B2 | 3/2009 | Shimmick |
| 7,508,525 B2 | 3/2009 | Zhou et al. |
| 7,535,577 B2 | 5/2009 | Podoleanu et al. |
| 7,537,591 B2 | 5/2009 | Feige et al. |
| 7,557,928 B2 | 7/2009 | Ueno |
| 7,575,322 B2 | 8/2009 | Somani |
| 7,593,559 B2 | 9/2009 | Toth et al. |
| 7,602,500 B2 | 10/2009 | Izatt et al. |
| 7,604,351 B2 | 10/2009 | Fukuma et al. |
| 7,614,744 B2 | 11/2009 | Abe |
| 7,630,083 B2 | 12/2009 | de Boer et al. |
| 7,631,970 B2 | 12/2009 | Wei |
| 7,633,627 B2 | 12/2009 | Choma et al. |
| 7,643,152 B2 | 1/2010 | de Boer et al. |
| 7,797,119 B2 | 9/2010 | De Boer et al. |
| 7,813,644 B2 | 10/2010 | Chen et al. |
| 7,898,712 B2 | 3/2011 | Adams et al. |
| 8,262,646 B2 | 9/2012 | Frey et al. |
| 8,394,084 B2 | 3/2013 | Palankar et al. |
| 2001/0022648 A1 | 9/2001 | Lai |
| 2002/0013574 A1 | 1/2002 | Elbrecht et al. |
| 2002/0082466 A1 | 6/2002 | Han |
| 2002/0097374 A1 | 7/2002 | Payne et al. |
| 2002/0133145 A1 | 9/2002 | Gerlach et al. |
| 2002/0198516 A1 | 12/2002 | Knopp |
| 2003/0090674 A1 | 5/2003 | Zeylikovich et al. |
| 2003/0206272 A1 | 11/2003 | Cornsweet et al. |
| 2004/0039378 A1 | 2/2004 | Lin |
| 2004/0059321 A1 | 3/2004 | Knopp et al. |
| 2004/0151466 A1 | 8/2004 | Crossman-Bosworth et al. |
| 2004/0243233 A1 | 12/2004 | Phillips |
| 2005/0010109 A1 | 1/2005 | Faul |
| 2005/0015120 A1 | 1/2005 | Seibel et al. |
| 2005/0021011 A1 | 1/2005 | LaHaye |
| 2005/0024586 A1 | 2/2005 | Teiwes et al. |
| 2005/0173817 A1 | 8/2005 | Fauver et al. |
| 2005/0192562 A1 | 9/2005 | Loesel et al. |
| 2005/0201633 A1 * | 9/2005 | Moon et al. ............... 382/268 |

(56) References Cited

U.S. PATENT DOCUMENTS

| | | | |
|---|---|---|---|
| 2005/0203492 A1 | 9/2005 | Nguyen et al. | |
| 2005/0215986 A1 | 9/2005 | Chernyak et al. | |
| 2005/0284774 A1 | 12/2005 | Mordaunt | |
| 2005/0286019 A1 | 12/2005 | Wiltberger et al. | |
| 2005/0288745 A1 | 12/2005 | Andersen et al. | |
| 2006/0020172 A1 | 1/2006 | Luerssen et al. | |
| 2006/0077346 A1 | 4/2006 | Matsumoto | |
| 2006/0100613 A1 | 5/2006 | McArdle et al. | |
| 2006/0179992 A1 | 8/2006 | Kermani | |
| 2006/0187462 A1* | 8/2006 | Srinivasan et al. | 356/479 |
| 2006/0195076 A1* | 8/2006 | Blumenkranz et al. | 606/4 |
| 2006/0206102 A1 | 9/2006 | Shimmick | |
| 2007/0013867 A1 | 1/2007 | Ichikawa | |
| 2007/0121069 A1 | 5/2007 | Andersen et al. | |
| 2007/0126985 A1 | 6/2007 | Wiltberger et al. | |
| 2007/0129709 A1 | 6/2007 | Andersen et al. | |
| 2007/0129775 A1 | 6/2007 | Mordaunt et al. | |
| 2007/0147730 A1 | 6/2007 | Wiltberger et al. | |
| 2007/0173791 A1 | 7/2007 | Raksi | |
| 2007/0173794 A1 | 7/2007 | Frey et al. | |
| 2007/0173795 A1 | 7/2007 | Frey et al. | |
| 2007/0185475 A1 | 8/2007 | Frey et al. | |
| 2007/0189664 A1 | 8/2007 | Andersen et al. | |
| 2007/0216909 A1* | 9/2007 | Everett et al. | 356/479 |
| 2007/0219541 A1 | 9/2007 | Kurtz | |
| 2007/0230520 A1 | 10/2007 | Mordaunt et al. | |
| 2007/0282313 A1* | 12/2007 | Huang et al. | 606/5 |
| 2007/0291277 A1* | 12/2007 | Everett et al. | 356/497 |
| 2007/0299429 A1 | 12/2007 | Amano | |
| 2008/0033406 A1 | 2/2008 | Andersen et al. | |
| 2008/0049188 A1 | 2/2008 | Wiltberger et al. | |
| 2008/0055543 A1 | 3/2008 | Meyer et al. | |
| 2008/0056610 A1* | 3/2008 | Kanda | 382/282 |
| 2008/0071254 A1 | 3/2008 | Lummis et al. | |
| 2008/0088795 A1 | 4/2008 | Goldstein et al. | |
| 2008/0100612 A1* | 5/2008 | Dastmalchi et al. | 345/418 |
| 2008/0281303 A1 | 11/2008 | Culbertson et al. | |
| 2008/0281413 A1 | 11/2008 | Culbertson et al. | |
| 2008/0319427 A1 | 12/2008 | Palanker | |
| 2009/0012507 A1 | 1/2009 | Culbertson et al. | |
| 2009/0088734 A1 | 4/2009 | Mordaunt | |
| 2009/0125005 A1* | 5/2009 | Chernyak et al. | 606/5 |
| 2009/0131921 A1 | 5/2009 | Kurtz et al. | |
| 2009/0149742 A1 | 6/2009 | Kato et al. | |
| 2009/0157062 A1* | 6/2009 | Hauger et al. | 606/5 |
| 2009/0161827 A1 | 6/2009 | Gertner et al. | |
| 2009/0168017 A1* | 7/2009 | O'Hara et al. | 351/205 |
| 2009/0177189 A1 | 7/2009 | Raksi | |
| 2009/0268161 A1* | 10/2009 | Hart et al. | 351/208 |
| 2010/0004641 A1 | 1/2010 | Frey et al. | |
| 2010/0004643 A1 | 1/2010 | Frey et al. | |
| 2010/0007848 A1* | 1/2010 | Murata | 351/206 |
| 2010/0022994 A1 | 1/2010 | Frey et al. | |
| 2010/0022995 A1 | 1/2010 | Frey et al. | |
| 2010/0022996 A1 | 1/2010 | Frey et al. | |
| 2010/0042079 A1 | 2/2010 | Frey et al. | |
| 2010/0110377 A1 | 5/2010 | Maloca et al. | |
| 2010/0324543 A1 | 12/2010 | Kurtz et al. | |
| 2011/0022036 A1 | 1/2011 | Frey et al. | |
| 2011/0118609 A1 | 5/2011 | Goldshleger et al. | |
| 2011/0196350 A1 | 8/2011 | Friedman et al. | |
| 2011/0202044 A1 | 8/2011 | Goldschleger et al. | |
| 2011/0222020 A1 | 9/2011 | Izatt et al. | |
| 2011/0304819 A1 | 12/2011 | Juhasz et al. | |
| 2011/0319873 A1 | 12/2011 | Raksi et al. | |
| 2012/0069302 A1 | 3/2012 | Juhasz et al. | |
| 2012/0274903 A1 | 11/2012 | Sayeram et al. | |

FOREIGN PATENT DOCUMENTS

| | | |
|---|---|---|
| JP | 4-503913 | 7/1992 |
| JP | 2002345758 | 12/2002 |
| JP | 2004-531344 | 10/2004 |
| JP | 2009-523556 | 6/2009 |
| UA | 8235 C2 | 3/1996 |
| WO | 90/09141 | 8/1990 |
| WO | 98/08048 | 2/1998 |
| WO | 03/002008 | 1/2003 |
| WO | 03/062802 | 7/2003 |
| WO | 2006/078802 | 7/2006 |
| WO | 2006074469 | 7/2006 |
| WO | 2007/084694 | 7/2007 |
| WO | WO2007106326 | 9/2007 |
| WO | 2007130411 | 11/2007 |
| WO | 2008/101359 | 8/2008 |
| WO | 2009/039302 | 3/2009 |
| WO | 2010/075571 | 7/2010 |
| WO | 2011103357 A2 | 8/2011 |
| WO | 2011159627 A2 | 12/2011 |

OTHER PUBLICATIONS

Kim, Tae Hoon, Authorized Officer, Korean Intellectual Property Office, PCT International Application No. PCT/US2011/023710, in International Search Report, mailed Aug. 24, 2011, 8 pages.

Eurepean Patent Office, European Patent Application No. 10191057.8, in European Search Report, mailed Mar. 16, 2011, to be published by the USPTO, 3 pages.

RE 90/006,816, filed Feb. 27, 2007, Swanson et al.

Chinn, S.R., et al., "Optical coherence tomography using a frequency-tunable optical source," Optics Letters, 22(5):340-342, Mar. 1997.

Huber, R., et al., "Three-dimensional and C-mode OCT imaging with a compact, frequency swept laser source at 1300 nm," Optics Express, 13(26):10523-10538, Dec. 2005.

Massow, O., et al., "Femtosecond laser microsurgery system controlled by optical coherence tomography," Proceedings of the SPIE—Commercial and Biomedical Applications of Ultrafast Lasers VIII, vol. 6881, pp. 688106(1)-688106(6), Mar. 2008.

Massow, O., et al., "Optical coherence tomography controlled femtosecond laser microsurgery system," Proceedings of the SPIE—Optical Coherence Tomography and Coherence Techniques III, vol. 6627, pp. 662717(1)-662717(6), Aug. 2007.

Ohmi, M., et al., "In-situ Observation of Tissue Laser Ablation Using Optical Coherence Tomography," Optical and Quantum Electronics, 37(13-15):1175-1183, Dec. 2005.

Sarunic, M., et al., "Imaging the Ocular Anterior Segment With Real-Time, Full-Range Fourier-Domain Optical Coherence Tomography," Archives of Ophthalmology, 126(4):537-542, Apr. 2008.

Sarunic, M., et al., "Instantaneous complex conjugate resolved spectral domain and swept-source OCT using 3×3 fiber couplers," Optics Express, 13(3):957-967, Feb. 2005.

Sarunic, M., et al., "Real-time quadrature projection complex conjugate resolved Fourier domain optical coherence tomography," Optics Letters, 31(16):2426-2428, Aug. 2006.

Swanson, et al., "Method and Apparatus for Optical Imaging with Means for Controlling the Longitudinal Range of the Sample," Re-exam U.S. Appl. No. 90/006,816, filed Oct. 20, 2003.

Tao, Y., et al., "High-speed complex conjugate resolved retinal spectral domain optical coherence tomography using sinusoidal phase modulation," Optics Letters, 32(20):2918-2920, Oct. 2007.

Yun, S.H., et al., "Wavelength-swept fiber laser with frequency shifted feedback and resonantly swept intra-cavity acoustooptic tunable filter," IEEE Journal of Selected Topics in Quantum Electronics, 3(4):1087-1096, Aug. 1997.

Arimoto et al., "Imaging Properties of Axicon in a Scanning Optical System," Nov. 1, 1992, Applied Optics, 31(31): 6652-6657, 5 pages.

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27, 7 pages.

Stern et al., "Femtosecond Optical Ranging of Corneal Incision Depth," Jan. 1989, Investigative Ophthalmology & Visual Science, 30(1):99-104, 6 pages.

Fercher et al., "Eye-Length Measurement by Interferometry With Partially Coherent Light," Mar. 1988, Optics Letters, 13(3):186-188, 3 pages.

(56) References Cited

OTHER PUBLICATIONS

Fercher et al., "Measurement of Intraocular Distances by Backscattering Spectral Interferometry," May 15, 1995, Optics Comm. 117:43-48, 6 pages.
Wojtkowski et al., "In Vivo Human Retinal Imaging by Fourier Domain Optical Coherence Tomography," Jul. 2002, Journal of Biomedical Optics 7(3):457-463, 7 pages.
Izatt et al., Micron-Resolution Biomedical Imaging With Optical Coherence Tomography, Oct. 1993, Optics & Photonics News, pp. 14-19, 6 pages.
Partial International Search Report corresponding to PCT Application Serial No. PCT/US2012/035927 dated Aug. 3, 2012.
Aslyo-Vogel et al., "Darstellung von LTK-Läsionen durch optische Kurzkohärenztomographie (OCT) und Polarisationsmikroskopie nach Sirius-Rot-Fäbung", Ophthalmologe, pp. 487-491, 7-97 , (1997).
Bagayev et al., "Optical coherence tomography for in situ monitoring of laser corneal ablation", Journal of Biomedical Optics, 7(4), pp. 633-642 (Oct. 2002).
Blaha et al., "The slit lamp and the laser in ophthalmology—a new laser slit lamp", SPIE Optical Instrumentation for Biomedical Laser Applications, vol. 658, pp. 38-42, 1986.
Boppart, S., et al., "Intraoperative Assessment of Microsurgery with Three-dimensional Optical Coherence Tomography", Radiology, 208(1):81-86, Jul. 1998.
Davidson, "Analytic Waveguide Solutions and the Coherence Probe Microscope", Microelectronic Engineering, 13, pp. 523-526, 1991.
Drexler, W., et al., "Measurement of the thickness of fundus layers by partial coherence tomography", Optical Engineering, 34(3):701-710, Mar. 1995.
Dyer, P., et al., "Optical Fibre Delivery and Tissue Ablation Studies using a Pulsed Hydrogen Fluoride Laser", Lasers in Medical Science, 7:331-340, 1992.
Fercher et al., "In Vivo Optical Coherence Tomography", American Journal of Ophthalmology, 116(1), pp. 113-114, 1993.
Fujimoto, J., et al., :Biomedical Imaging using Optical Coherent Tomography, 1994, 67.
Hammer, D., "Ultrashort pulse laser induced bubble creation thresholds in ocular media", SPIE, 2391:30-40, 1995.
Hauger, C., et al., "High speed low coherence interferometer for optical coherence tomography", Proceedings of SPIE, 4619:1-9, 2002.
Hee, M., et al., "Optical Coherence tomography of the Human Retina", Arch Ophthalmol, 113:325-332; Mar. 1995.
Hitzenberger et al., "Interferometric Measurement of Corneal Thickness With Micrometer Precision", American Journal of Ophthalmology, 118:468-476, Oct. 1994.
Hitzenberger, C., et al., "Retinal layers located with a precision of 5 µm by partial coherence interferometry", SPIE, 2393:176-181, 1995.
Itoh et al., "Absolute measurements of 3-D shape using white-light interferometer", SPIE Interferometry: Techniques and Analysis, 1755:24-28, 1992.
Izatt et al., "Ophthalmic Diagnostics using Optical Coherence Tomography", SPIE Ophthalmic Technologies, 1877:136-144, 1993.
Izatt, J., et al., "Micrometer-Scale Resolution Imaging of the Anterior Eye In vivo With Optical Coherence Tomography", Arch Ophthalmol, 112:1584-1589, Dec. 1994.
Jean, B., et al., "Topography assisted photoablation", SPIE, vol. 3591:202-208, 1999.
Kamensky, V., et al., "In Situ Monitoring of Laser Modification Process in Human Cataractous Lens and Porcine Cornea Using Coherence Tomography", Journal of biomedical Optics, 4(1), 137-143, Jan. 1999.
Lee et al., "Profilometry with a coherence scanning microscope", Applied Optics, 29(26), 3784-3788, Sep. 10, 1990.
Lubatschowski, "The German Ministry of Research and education funded this OCT guided fs laser surgery in Sep. 2005", http://www.laser-zentrum-hannover.de/download/pdf/taetigkeitsbericht2005.pdf.
Massow, O., et al., "Femtosecond laser microsurgery system controlled by OCT", Laser Zentrum Hannover e.V., The German Ministry of education and research,19 slides, 2007.
Puliafito, Carmen, "Final technical Report: Air Force Grant #F49620-93-I-03337(1)" dated Feb. 12, 1997, 9 pages.
Ren, Q., et al., "Axicon: A New Laser Beam Delivery System for Corneal Surgery", IEEE Journal of Quantum Electronics, 26(12):2305-2308, Dec. 1990.
Ren, Q., et al., "Cataract Surgery with a Mid-Infrared Endo-laser System", SPIE Ophthalmic Technologies II, 1644:188-192, 1992.
Thompson, K., et al., "Therapeutic and Diagnostic Application of Lasers in Ophthalmology", Proceedings of the IEEE, 80(6):838-860, Jun. 1992.
Thrane, L, et al., "Calculation of the maximum obtainable probing depth of optical coherence tomography in tissue", Proceedings of SPIE, 3915:2-11, 2000.
Wisweh, H., et al., "OCT controlled vocal fold femtosecond laser microsurgery", Laser Zentrum Hannover e.V., The German Ministry of education and research, Grants: 13N8710 and 13N8712; 23 slides, 2008.
PCT International Search Report and Written Opinion dated Feb. 9, 2012 for International Application Serial No. PCT/US2011/040223.
Hee et al.; "Femtosecond transillumination optical coherence tomography"; Optics Letters; vol. 18; No. 12; pp. 950-952 (Jun. 1993).
Kamensky et al.; "In situ monitoring of the middle IR laser ablation of a cataract-suffered human lens by optical coherent tomography"; Proc. SPIE; 2930: 222-229 (1996).
Kamensky et al.; "Monitoring and animation of laser ablation process in cataracted eye lens using coherence IDS 41 tomography"; Proc. SPIE; 2981: 94-102 (1997).
Ostaszewski et al.; "Risley prism beam pointer"; Proc. of SPIE; vol. 6304; 630406-1 through 630406-10, (2006).
PCT International Search Report for International Application Serial No. PCT/US2010/056701 mailed Aug. 24, 2011.
Swanson et al.; "In vivo retinal imaging by optical coherence tomography"; Optics Letters; vol. 18; No. 21; pp. 1864-1866 (Nov. 1993).
PCT International Search Report and Written Opinion dated Apr. 10, 2012 for International Application No. PCT/US2011/051466, filed Sep. 13, 2011.

* cited by examiner

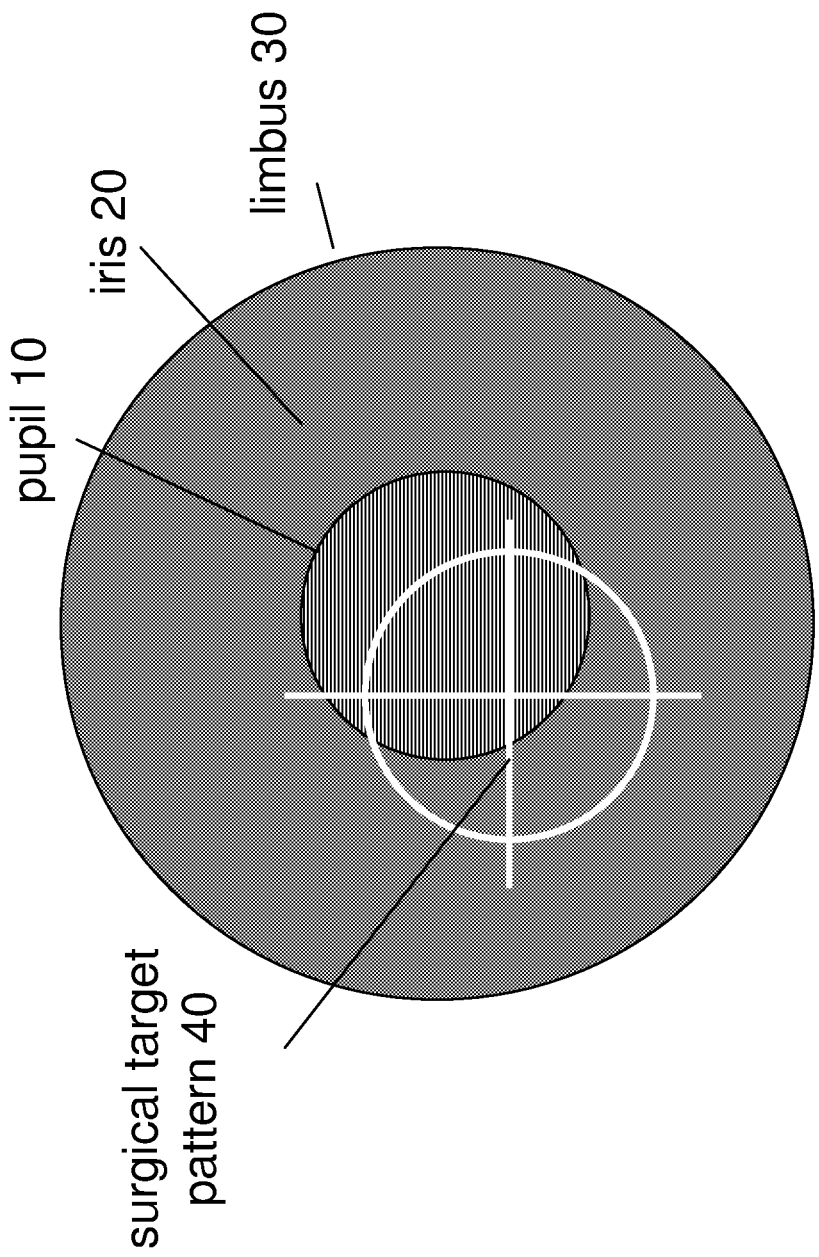

IMAGING SURGICAL TARGET TISSUE BY NONLINEAR SCANNING

TECHNICAL FIELD

This patent document relates to systems and techniques for surgical applications, including ophthalmic surgery.

BACKGROUND

A variety of advanced surgical laser systems have been developed over the years for ophthalmic surgery, targeting portions of the cornea, the lens, the retina and other structures of the eye. Such a surgical system can employ an imaging mechanism to obtain images of a targeted surgical region to assist the operator of the surgical system, e.g. the surgeon, to place laser pulses in the targeted surgical region of the eye with high precision.

SUMMARY

This document discloses examples and implementations of systems and techniques for laser surgery based on imaging a target tissue by nonlinear scanning during the imaging.

For example, a method for guiding an eye surgery can include the steps of: positioning an eye in relation to an imaging system; creating first scan data by determining a depth of an eye target region at a first set of points along a first arc; creating second scan data by determining a depth of the eye target region at a second set of points along a second arc; determining target region parameters based on the first and second scan data; and adjusting one or more surgical position parameters according to the determined target region parameters.

In some implementations, the determining the depth includes imaging the eye target region with at least one of an optical coherence tomography (OCT) method, an ultrasound-based method, a microscopic method and an interference based method.

In some implementations, the eye target region is one of a corneal target region, an anterior lens surface, a posterior lens surface, a lens target region, an ophthalmic layer, and a surface defined by a pupil.

In some implementations, at least one of the first arc and the second arc forms at least part of a closed loop.

In some implementations, the first arc is a portion of a first intersection line where a first scanning surface intersects the eye target region; and the second arc is a portion of a second intersection line where a second scanning surface intersects the eye target region.

In some implementations, the first arc is a portion of a first intersection line where a first cylinder intersects the eye target region; and the second arc is a portion of a second intersection line where a second cylinder intersects the eye target region.

In some implementations, the first cylinder and the second cylinder are concentric, sharing a Z axis.

In some implementations, a Z axis of the second cylinder is offset from a Z axis of the first cylinder.

In some implementations, the determining target region parameters step includes extracting scan characteristics from the first and second scan data.

In some implementations, the extracting scan characteristics step includes extracting a first amplitude and a first phase of the first scan data; and extracting a second amplitude and a second phase of the second scan data.

In some implementations, the determining of target region parameters step includes determining a position parameter of a center of the target region based on the first amplitude, first phase, second amplitude and second phase.

In some implementations, the determining of the target region parameters step includes determining an object shape parameter of the target region based on the first amplitude, first phase, second amplitude and second phase.

In some implementations, the determining of the target region parameters step includes determining an object orientation parameter of the target region based on the first amplitude, first phase, second amplitude and second phase.

In some implementations, the determining of the target region parameters step includes determining a position parameter update, related to a position of the target region and a reference point.

In some implementations, the adjusting the surgical position parameter includes adjusting a position parameter of a surgical pattern center to align the surgical pattern center with a center of the target region.

In some implementations, the method contains no more scans after the first scan and the second scan.

In some implementations, the time from the starting of the first scanning step to the finishing of the determining the surgical position parameters step is no more than one of 100 milliseconds, 1,000 milliseconds and 10,000 milliseconds.

In some implementations, at least one of the first and second arc is elliptical.

In some implementations, at least one of the first arc and the second arc is an open arc; and at least one of the first scan data and the second scan data have a maximum and a minimum.

In some implementations, the eye target region is a region of a lens of the eye, the target region parameters include a shape parameter of the lens, a tilt parameter of the lens, and a position parameter of the lens.

In some implementations, the determining target region parameter step includes fitting a function with at least one fitting parameter to the first scan data; and determining the target region parameter using the fitting parameter.

In some implementations, a method for imaging an object includes the steps of positioning the object relative to an imaging system, wherein a shape of the object is describable in terms of one or more shape parameter; creating scan data by determining a coordinate of the object at a set of points along an arc; and determining an object shape parameter and an object position parameter based on the scan data.

In some implementations, the object is a portion of a spherical surface layer; and the determined object shape parameter is a radius of the spherical surface layer.

In some implementations, the object is an anterior lens surface layer of an eye; the object shape parameter is a radius of the anterior lens surface layer; and the object position parameter is a coordinate of a center of the anterior lens surface.

In some implementations, the determining the object position parameter step includes imaging the object with at least one of an optical coherence tomography (OCT) method, an ultrasound-based method, a microscopic method and an interference based method.

In some implementations, the determining the object shape parameter and the object position parameter step includes creating auxiliary scan data by determining a coordinate of the object at an auxiliary set of points along an auxiliary arc.

In some implementations, the determining the object shape parameter and the object position parameter step includes determining the object shape parameter and the object position parameter from the scan data and the auxiliary scan data.

In some implementations, the position parameter of the object is a Z coordinate of an object layer; and the arc is a portion of an intersection line where a scanning cylinder intersects the object layer.

In some implementations, the determining the object shape parameter step includes determining the Z coordinate of the object layer at the auxiliary set of points along an intersection line where an auxiliary cylinder intersects the object layer.

In some implementations, the scanning cylinder and the auxiliary cylinder are essentially concentric, sharing a Z axis.

In some implementations, the determining the object shape parameter and object position parameter step includes extracting an amplitude and a phase of the scan data; and determining a center of the object layer based on the extracted amplitude and phase.

In some implementations, the object position parameter is one of a parameter of a center of the object layer and a perimeter of the object layer.

In some implementations, the method contains no more scans after the scan and an auxiliary scan.

In some implementations, the determining of the object position parameter and the object shape parameter are performed in an integrated manner.

In some implementations the object is one of a closed object and an open object.

In some implementations, a method for guiding eye surgery includes the steps of (a) positioning an eye relative to a surgical laser system, the surgical laser system having a surgical position parameter and the eye having a lens; (b) determining position data of a lens target region along a scanning arc; (c) determining a lens position parameter based on the position data; (d) adjusting the surgical position parameter according to the determined lens position parameter; and (e) repeating steps (b)-(d) during the eye surgery to readjust the surgical position parameter.

In some implementations, the lens target is one of an anterior lens surface, an anterior surface defined by a pupil, a lens target region, and a posterior lens surface.

In some implementations, the determining of the lens position parameters step includes extracting an amplitude and a phase of the position data.

In some implementations, the determining of the lens position parameters step includes determining a position parameter of a center of the lens target based on the amplitude and phase of the position data.

In some implementations, the adjusting a surgical position parameter includes adjusting a position parameter of a surgical pattern center to align a surgical pattern in three dimensions with respect to a characteristic feature of the lens.

BRIEF DESCRIPTION OF THE DRAWINGS

FIGS. 1A-C illustrate a targeting offset in ophthalmic laser systems.

DETAILED DESCRIPTION

Many eye surgical devices include a docking stage, which makes contact with the eye and keeps it effectively immobile relative to the objective of the surgical system. To guide the surgical procedure, certain systems generate a target pattern, which indicates the center of the objective where the surgical laser is focused. These systems display the target pattern over the image of the eye to guide the surgeon to apply the laser beam precisely to the intended target region of the eye.

Figure 1B:
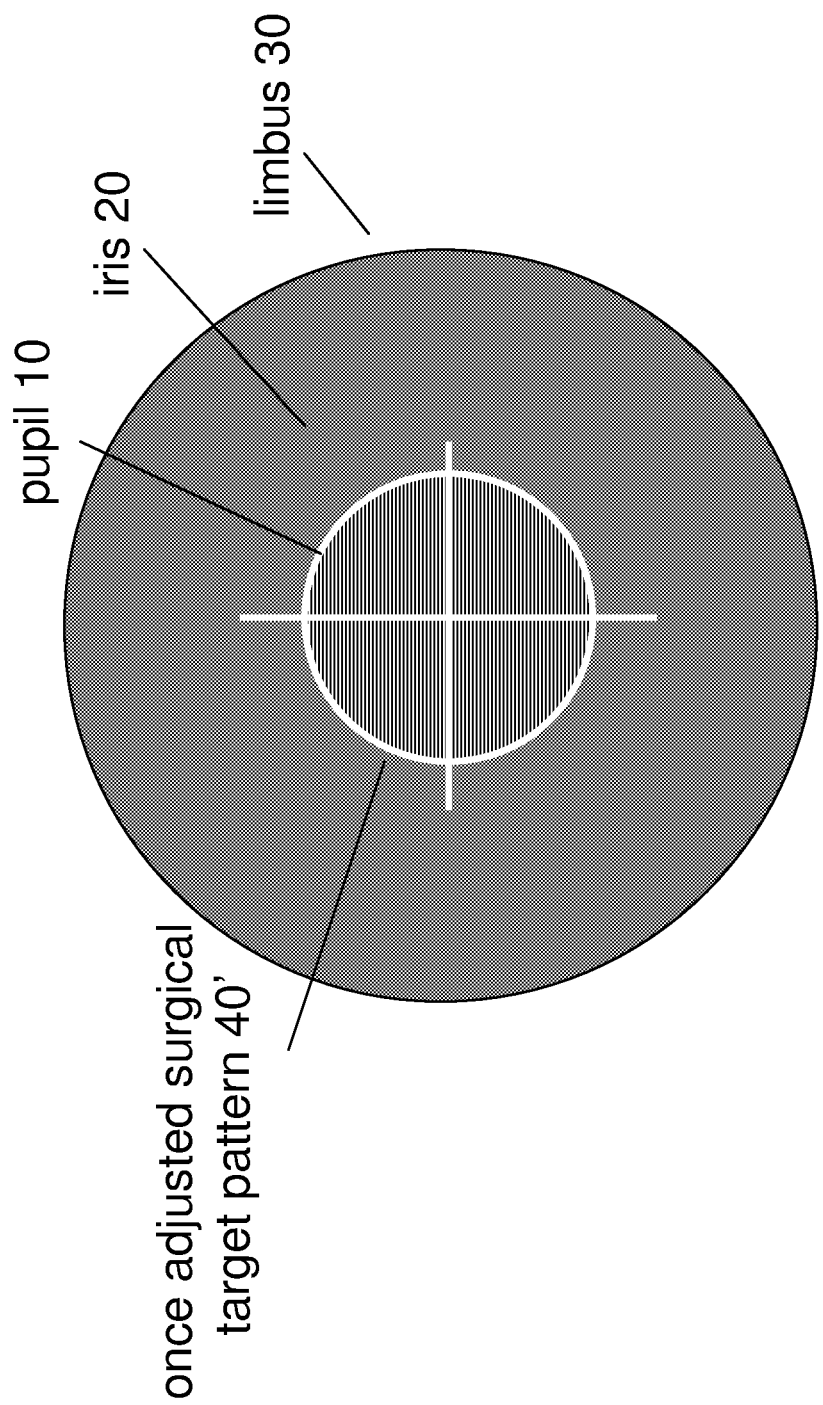

FIGS. 1A-B illustrate the operation of an example of such image guided surgical systems. When the docking stage or objective is docked to the eye by the surgeon, the target pattern 40 may not be centered perfectly relative to the eye so that the center of the target pattern 40 may have be offset in position from the center of the eye.

FIG. 1A illustrates such a case when the target pattern 40 is not well centered with any one of prominent structures of the eye, such as the pupil 10, the iris 20 or the limbus 30. This misalignment poses a difficulty for the eye surgeon to place the laser pulses with high precision on the intended target within the eye.

An advanced image guided surgical laser system may be designed to extract information about the degree of the misalignment and to adjust the location of the target pattern 40 to be centered relative to a selected eye structure, such as the pupil 10. FIG. 1B illustrates an adjusted alignment in such a system that essentially eliminates the offset shown in FIG. 1A. In such an advanced system the target pattern 40 can be shifted to the center, enabling a subsequent high precision application of the surgical laser beam.

The higher the precision of the targeting system, the more efficient the ophthalmic surgery. Therefore, while a manual adjustment of the target pattern 40 is possible, computer-based automated alignment adjustments can be used to improve the precision of image guided systems and to overcome the problem of the misalignment.

Figure 2:
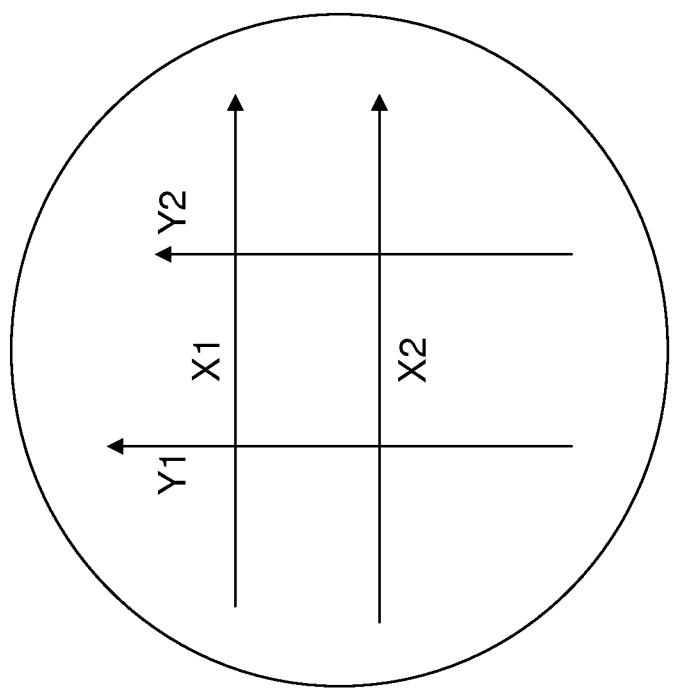
FIG. 2 illustrates an existing targeting method.

FIG. 2 illustrates the operation of one example of a computer-based automated alignment adjustment. In this example, scans are performed along straight lines, and the linear scans are performed repeatedly and iteratively. While each linear scan provides only incomplete information regarding the misalignment, the repeated iterations improve the guidance how to move the center of the target pattern 40 closer and closer to the center of the target region.

Examples and implementations of systems, apparatus and techniques are provided in this document for laser surgery based on imaging a target tissue by nonlinear scanning during the imaging. The imaging information obtained from the nonlinear scanning is used to guide the laser beam for performing the laser surgery on the target tissue.

Figure 3:
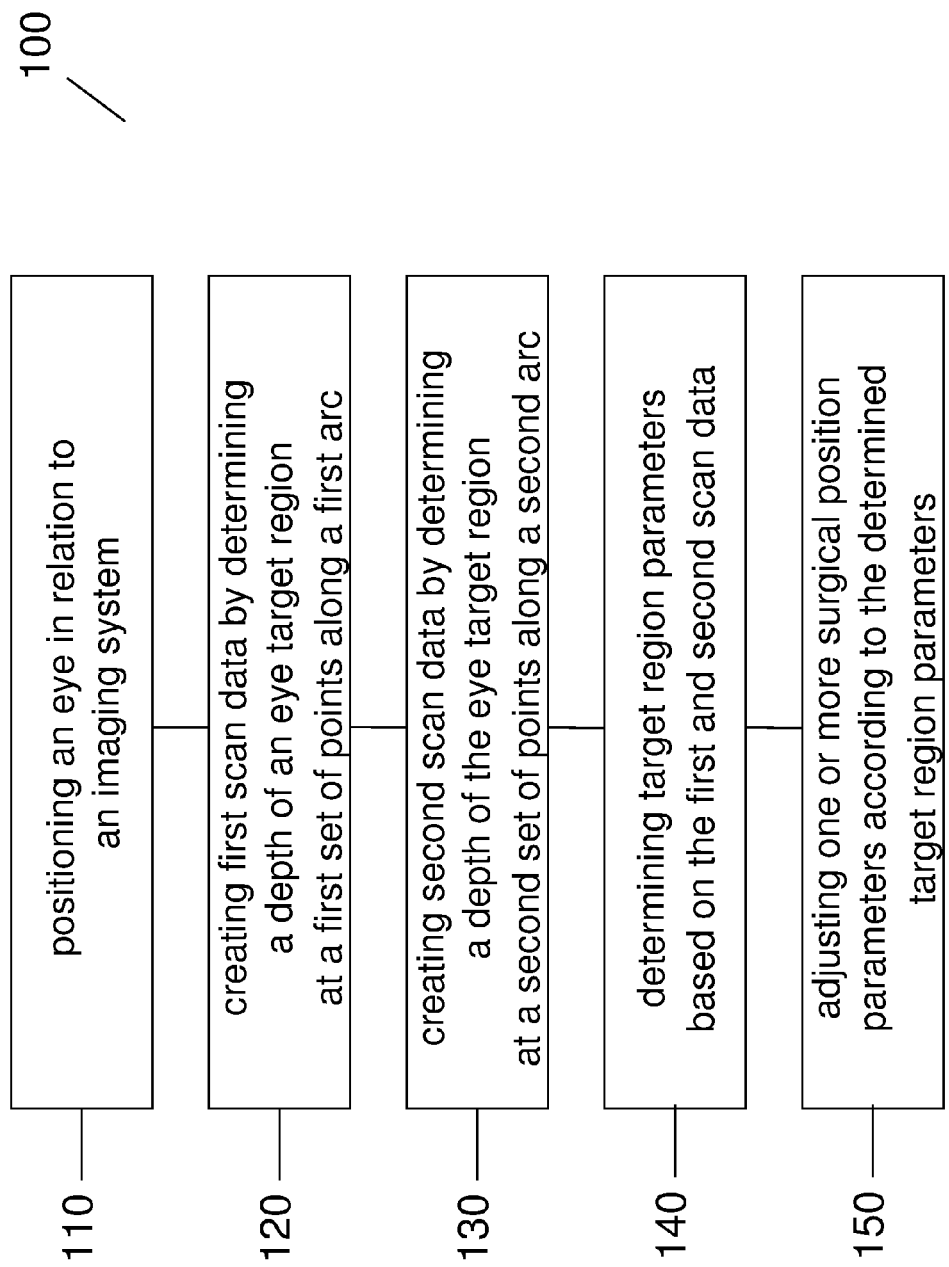
FIG. 3 illustrates an embodiment of a method to guide an eye surgery.

FIG. 3 illustrates a method for guiding an eye surgery 100, which includes the steps of: positioning an eye in relation to an imaging system 110; creating first scan data by determining a depth of an eye target region at a first set of points along a first arc 120; creating second scan data by determining the depth of the eye target region at a second set of points along a second arc 130; determining target region parameters based on the first and second scan data 140; and adjusting one or more surgical position parameters according to the determined target region parameters 150.

The positioning step 110 can include a wide variety of known methods, including applying a suitable type of a patient interface. One possibility is to lower a gantry supporting a patient interface and an objective of the surgical system onto the eye.

The patient interface can have a flexible skirt, partially made of an elastic material, surrounding an optical targeting system of a surgical system, such as the objective. The patient interface can include suction cups. Once the patient interface has been positioned on the eye, vacuum can be applied under the flexible skirt of the suction cup to establish a mechanical connection and stabilizing force between the eye and the patient interface. The suction cup can apply the vacuum to a large portion of the eye or to a ring-like region of the eye.

In other implementations, the patient interface can include a corrugated surface, which establishes a grip on the eye by making small and gentle indentations into the surface of the eye. These embodiments may position the eye without applying a vacuum. Yet other embodiments can apply some degree of pressure to establish a mechanical connection. Embodiments can establish the mechanical connection via a portion of the eye: within a surgical region, around a perimeter of the surgical region, or an outer region of the eye. Some embodiments may position the eye by other means, including non-mechanical connections.

The degree of the mechanical connection can be of widely varying type: in some implementations the eye can be firmly connected to the patient interface, preventing motion of the eye relative to the patient interface. In other embodiments, the connection can be of intermediate strength, allowing some degree of relative motion of the eye. In some cases certain type of relative motion can be allowed, such as motion along an optical axis, or transverse to the optical axis. In some embodiments, the positioning may not involve direct mechanical contact to a patient interface.

The positioning can also include varying degrees of applanation of the eye contact surface. In some cases the contact surface of the eye is essentially flattened, in others the contact surface can be only partially flattened, and in yet others the natural curvature of the eye may remain essentially unchanged.

Referring back to FIGS. 1A-C, the eye surgical procedure can utilize a surgical target pattern 40. The reference framework defined by this target pattern 40 can be used by the surgeon to direct a surgical laser beam to a precisely defined location within the surgical region of the eye. The target pattern 40 can be displayed e.g. on a video-microscope or an other type of display device. The target pattern 40 can be shown overlaid with the image of the eye on the video-microscope. In other embodiments, the target pattern 40 can be only a construct of a software program, not necessarily displayed anywhere. In some of these embodiments, the software may only track the center of the target pattern 40 and can guide the surgeon based on the location of the center. In semi-, or fully automatic embodiments the software of the system can carry out the guiding steps described below, without ever displaying an explicit target pattern 40.

At the start of the surgical proceedings, the target pattern 40 may be centered at the physical or geometrical center of the patient interface or the objective. Since the patient interface can be rarely positioned and docked to be perfectly aligned with the center of the eye in step 110, the target pattern 40 typically needs shifting or adjustment after the positioning/docking so that it is aligned well with a center of the eye or with an identifiable structure of the eye. Here the center of the eye may refer to a center of a selected structure of the eye, including the pupil 10, the iris 20, the limbus 30, or the lens 50. The identifiable structure can be an identifiable limbic structure, blood vessel, the fovea, the optic disc or another structure.

The eye structures, such as the lens 50 and the pupil 10 often do not share a common center. This can occur e.g. because of some inherent asymmetry of the eye, or because the pressure from the patient interface may have moved or tilted the lens 50 relative to the pupil 10.

Figure 1C:
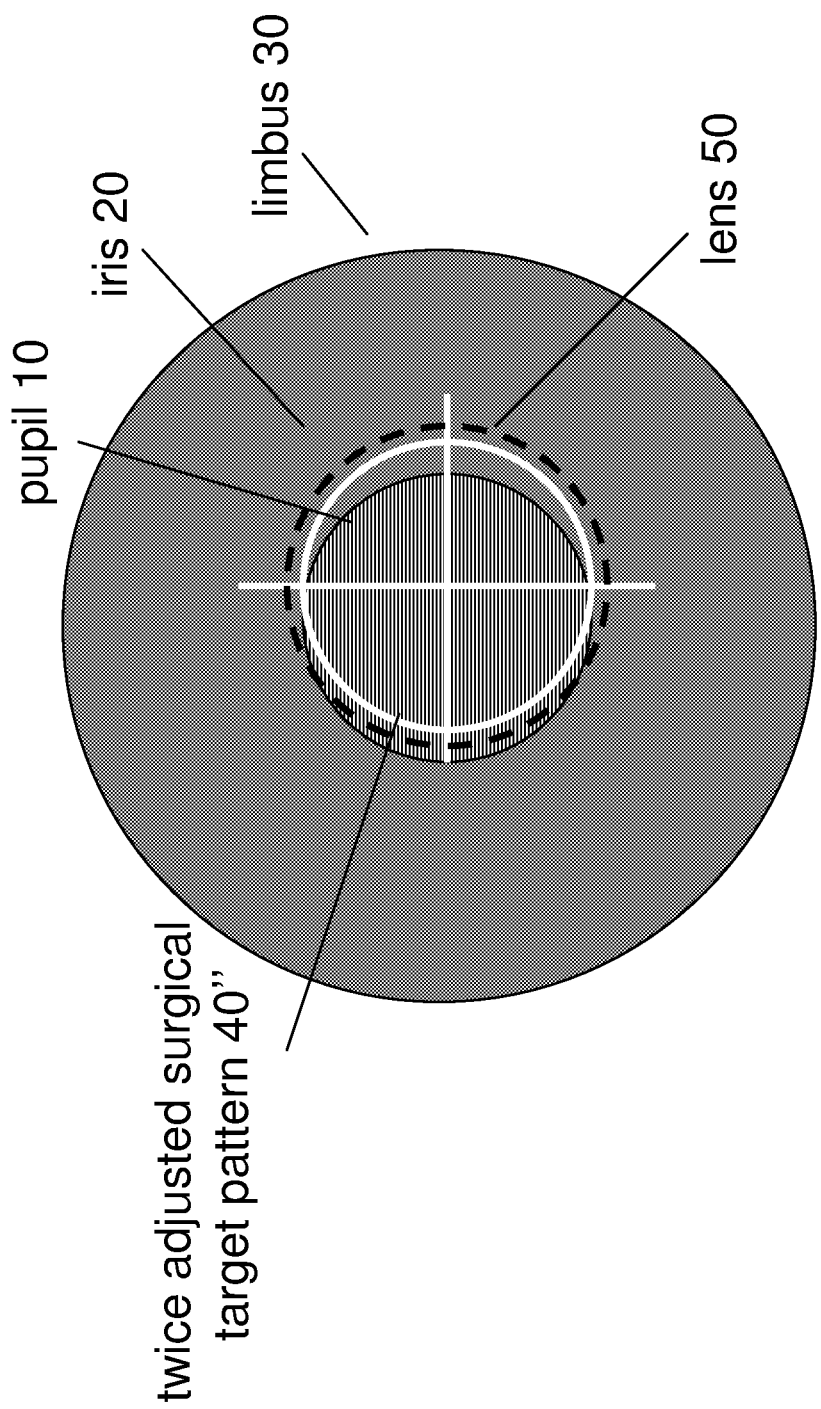

FIGS. 1A-C illustrate that in this typical situation the operator of the imaging system may perform a first shift of the target pattern 40 from its initial, off-center position in FIG. 1A to be aligned with a prominent eye structure, such as the pupil 10, indicated by once shifted target pattern 40' in FIG. 1B. This can be done manually or in a partially or fully automated manner. In ophthalmic procedures which target the lens 50, if the pupil 10 and the lens 50 share a center, then centering the target pattern 40 to the pupil 10 completes the adjusting method and the surgeon can use this once shifted target pattern 40' to guide the lens surgery.

FIG. 1C illustrates the case when the lens 50 is not aligned with the pupil 10. In this case, after the first shift of the target pattern 40' to align it with the pupil 10, in a subsequent second step the operator can practice the guiding method 100 to identify how much the once shifted center of the target pattern 40' and the pupil 10 is still off the center of the lens 50, and perform a second shift of the target pattern 40' to be aligned with the center of the lens 50, as shown by twice shifted target pattern 40" in FIG. 1C.

In some implementations, the first and the second shift of the target pattern 40 can be performed in a single integrated step by practicing the guiding method 100 to shift the target pattern 40 from its initial "as-docked" position to the center of the lens 50.

Once the target pattern 40 is aligned with the targeted surgical region, such as centered to the center of the lens 50, a surgical laser can be applied to perform a surgery on the lens 50 using the reference frame of the target pattern 40.

A location of the target pattern 40 can be stored e.g. in a computer controller of the surgical system. In some implementations, a video interface may overlay an image of the target pattern 40 and an actual image of the eye on a video microscope. Among others, such a composite picture illustrates the degree of the de-center of the target pattern 40 from a center of a selected eye structure, such as the pupil 10. Such overlaid composite images can be helpful to perform the first shift, aligning the target pattern 40 with e.g. the pupil 10.

It is noted that the first and second shifts (or the integrated single shift) move the target pattern 40 away from the center of the patient interface or the objective. With a sufficiently good design of the surgical optics, the subsequently applied surgical lasers may preserve their low astigmatism and other aberrations even when applied to this shifted off-center target region.

Examples of surgical procedures which benefit from a precisely targeted surgical laser include capsulotomy, i.e. cutting a circle into the capsule of the lens 50 for the purpose of inserting an Intra Ocular Lens (IOL) in place of a removed existing lens. A high precision centering of the capsulotomy cut allows a high precision centering of the inserted Intra Ocular Lens (IOL), optimizing the outcome of the cataract surgery.

Another example is the fragmentation or liquefication of the lens itself, which is performed in preparation for the removal of the lens from the lens capsule. In general, it is beneficial to remove as large a fraction of the lens as possible, while making sure not to puncture the posterior surface of the lens capsule. A low precision targeting system may force the surgeon to leave a thicker layer of the lens in the capsule just to make sure not to puncture the posterior capsule surface. In contrast, a system which positions the target pattern 40 with high precision can allow cutting very close to the posterior capsule surface, improving the efficiency of the cataract surgery.

It is noted that the target pattern 40 can be one of a wide variety of patterns, including one or multiple concentric circles, a cross-hair pattern, another indication of a center of the pattern, or one or more rectangular elements, and a combination of the above. The pattern may have variable elements, e.g. one of the lines can change color, or additional lines may appear to indicate any of the steps of the method, such as the successful completion of the positioning of the eye in step 110, or the successful readjusting of the surgical positions parameters in step 150.

It is further noted that the application of the surgical laser can follow a surgical pattern, which can be different from the target pattern in general. The surgical pattern can be a very wide variety of patterns, including circles, cylinders, sequential layers, spirals, 4, 6, or 8 fold radial partitioning, and other chopping patterns. In the context of the present guiding method 100, the position of this surgical pattern can be adjusted according to the shifted target pattern in step 150. In the simplest case, the center of the surgical pattern can be aligned with the center of the target pattern 40. But a wide variety of alternative adjustments are also possible, such as centering the surgical pattern with a shift relative to the center of the target pattern 40, or placing a starting location of the surgical pattern to a specific point of the target pattern, etc.

In some implementations, the determining the depth in steps 120 and 130 can include: imaging the eye target region with an optical coherence tomography (OCT) method, an ultrasound-based method, a microscopic method and an interference based method, or a combination of these methods. The optical coherence tomography method can be implemented as a time domain or a frequency domain tomography.

In some of the subsequent sections, the guiding method 100 will be described in the context of performing the above described second shift or integrated shift of the target pattern 40. Both implementations involve determining the misalignment of the target pattern 40 and the center of the eye target region, such as the lens 50.

The eye target region can be a corneal target region, an anterior lens surface, a posterior lens surface, a lens target region, an ophthalmic layer, or a surface defined by a pupil. The term "surface" is used in a broad sense, referring not only to an outermost geometrical surface, but to surface layers with some thickness. Surface layers can be defined e.g. by their biological, optical or mechanical properties and can have a layer thickness from a micron or less to a millimeter or more. Also, the term "layer" can refer to a layer inside a structure of the eye.

The surgical regions may be targeted in various ophthalmic surgical procedures, including corneal procedures, cataract procedures, capsulotomy, lens lysis or fragmentation. The target region can be the target region of the ophthalmic procedure itself, such as a lens surface, or an auxiliary target region, e.g. a region where an access cut is created on the cornea to facilitate a lens procedure.

Figure 4A:
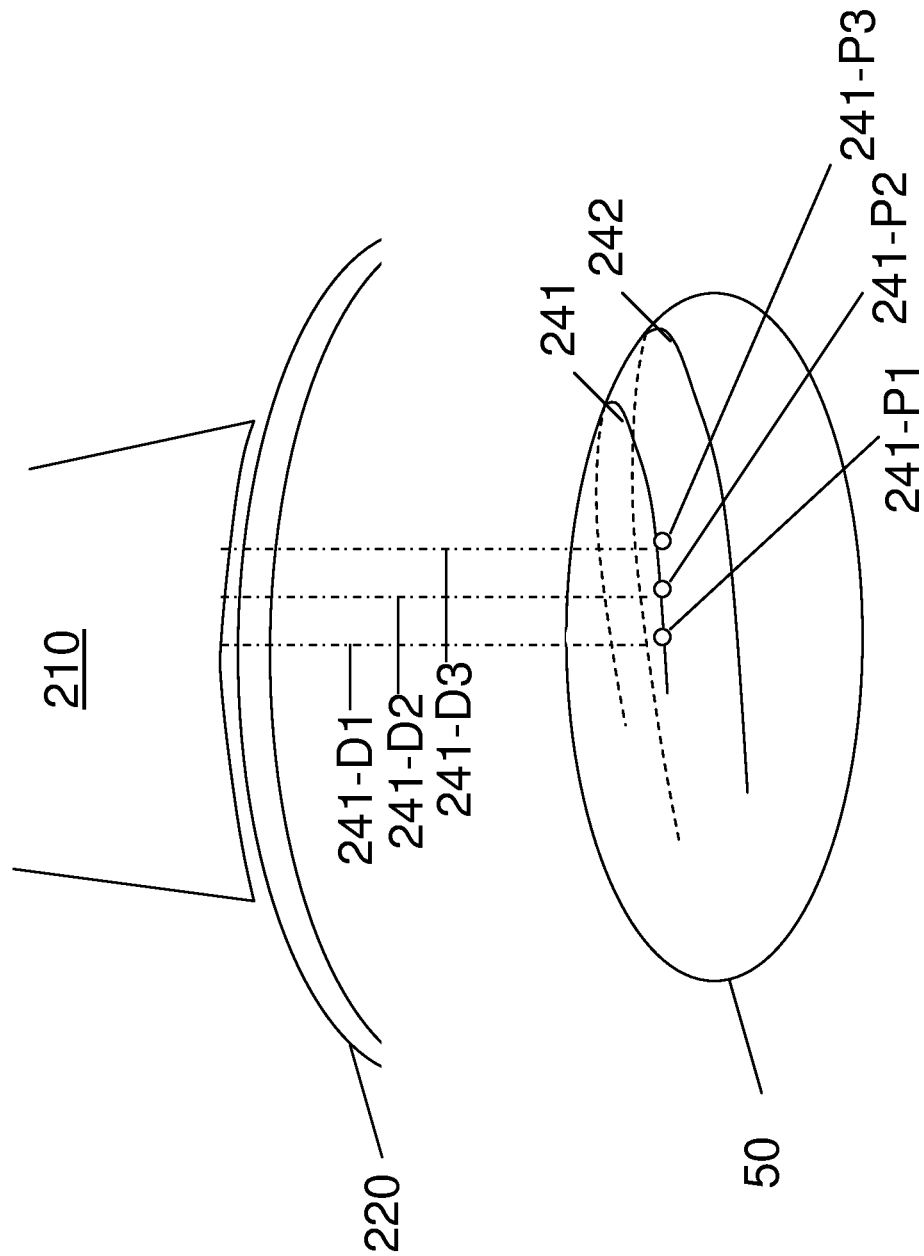
FIGS. 4A-E illustrate the steps of the method of FIG. 3.

FIG. 4A illustrates an implementation of method 100. In step 110 a patient interface 210 can be brought into mechanical contact with a cornea 220 of an eye to position the eye for an ophthalmic surgery. For example, the patient interface 210 can immobilize the eye and its cornea 220 by applying a partial vacuum.

The step 120 can include determining a depth 241-D1, . . . 241-Dn of an eye target region in the lens 50 at a first set of points 241-P1, . . . 241-Pn along a first arc 241 and storing the depth values 241-D as the first scan data.

The analogous step 130 can involve determining a depth 242-D1, . . . 242-Dn at a second set of points 242-P1, . . . 242-Pn along a second arc 242 and storing the depth values 242-D as the second scan data.

In some implementations, at least one of the first and the second arcs can be part of or the entirety of a closed loop. The loop can be a circle, an ellipse, a partially irregular loop, or a suitably shaped loop. In other implementations the arc can be an open arc, which is a portion of a circle, ellipse, or other suitable curve.

In some implementations, the arcs, or open or closed loops, 241 and 242 can be centered at the center of the target pattern 40. Therefore, after the offset of the center of the loops 241 and 242 from the center of the target region is determined, the center of the target pattern 40 can be aligned with the center of the target region by shifting the center of the target pattern 40 by the offset of the loops 241 and 242. In several of the below embodiments the first and second arcs 241, 242 share a center with the target pattern 40.

Arcs can be a wide variety of lines, distinguished from the straight lines of FIG. 2 by their non-negligible curvature in the XY plane, i.e. the plane transverse to the optical axis (commonly referred to as the Z axis). It is noted that even the straight lines of FIG. 2 may have some curvature in planes containing e.g. the Z and X, or Z and Y axes. However, since they appear as straight lines on a view of the XY plane, i.e. when projected onto the XY plane, they will not be termed an arc.

Figure 4B:
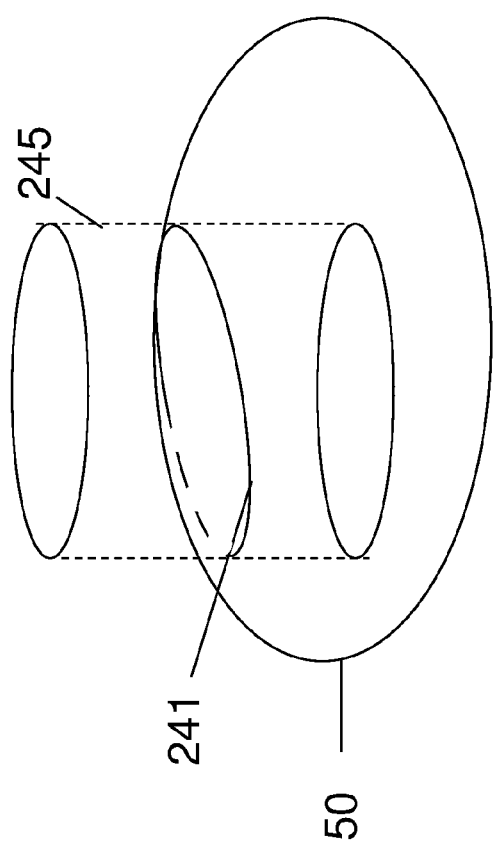

FIG. 4B illustrates that in some embodiments, the first arc 241 can be a portion of a first intersection line where a first scanning surface 245 intersects an eye target region, e.g. the anterior surface region of the lens 50. Analogously, the second arc 242 can be a portion of a second intersection line where a second scanning surface intersects the eye target region.

Here the scanning surface 245 can refer to the surface swept by a scanning beam as a characteristic point of the scanning beam, such as its focus point, is moved along a line in the target region.

In the example of FIG. 4B, a focal point of a scanning laser beam can be moved along a circle in an XY plane. The scanning laser can be essentially parallel to the optical Z axis of the optical system, defining a cylinder as the scanning surface 245. Visibly, in this example the first arc 241 is the loop where the cylindrical scanning surface 245 intersects the ellipsoidal lens 50. Depending on the position of the center of the cylindrical scanning surface 245, the first arc 241 can be a circle or an ellipse. The plane of the circle or ellipse 241 can be transverse to the Z axis, i.e. it can be the XY plane, if the center of the circle 241 coincides with that of the lens 50. In other words, if the circle 241 shares the symmetry axis with the lens 50. If the circle 241 does not share its symmetry axis with the lens 50, or equivalently the center of the circle 241 does not coincide with the center of the lens 50, then the plane of the circle 241 can be tilted, as in FIG. 4B.

Figure 4C:
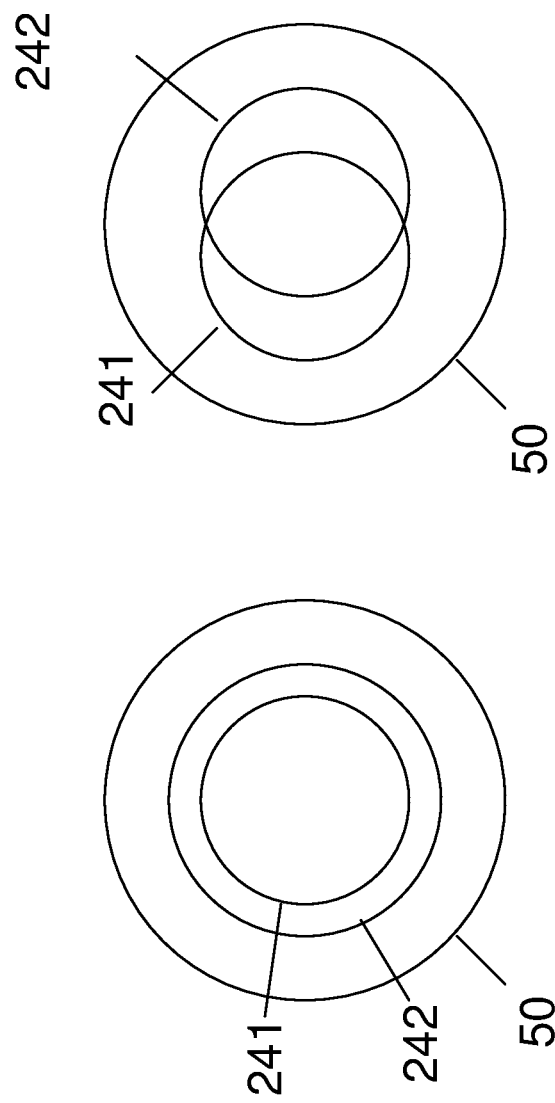

FIG. 4C illustrates embodiments where the first and second arcs 241 and 242 are closed loops, e.g. circles. In the left panel the first and second scanning cylinders and their corresponding loops 241 and 242 are concentric, sharing an optical, or Z axis. In the right panel, the loops 241 and 242 are not concentric, having their axes offset relative to each other. They may or may not intersect each other. Different embodiments may extract target-center-adjustment information better from concentric scanning circles, while others from offset scanning circles.

Figure 4D:
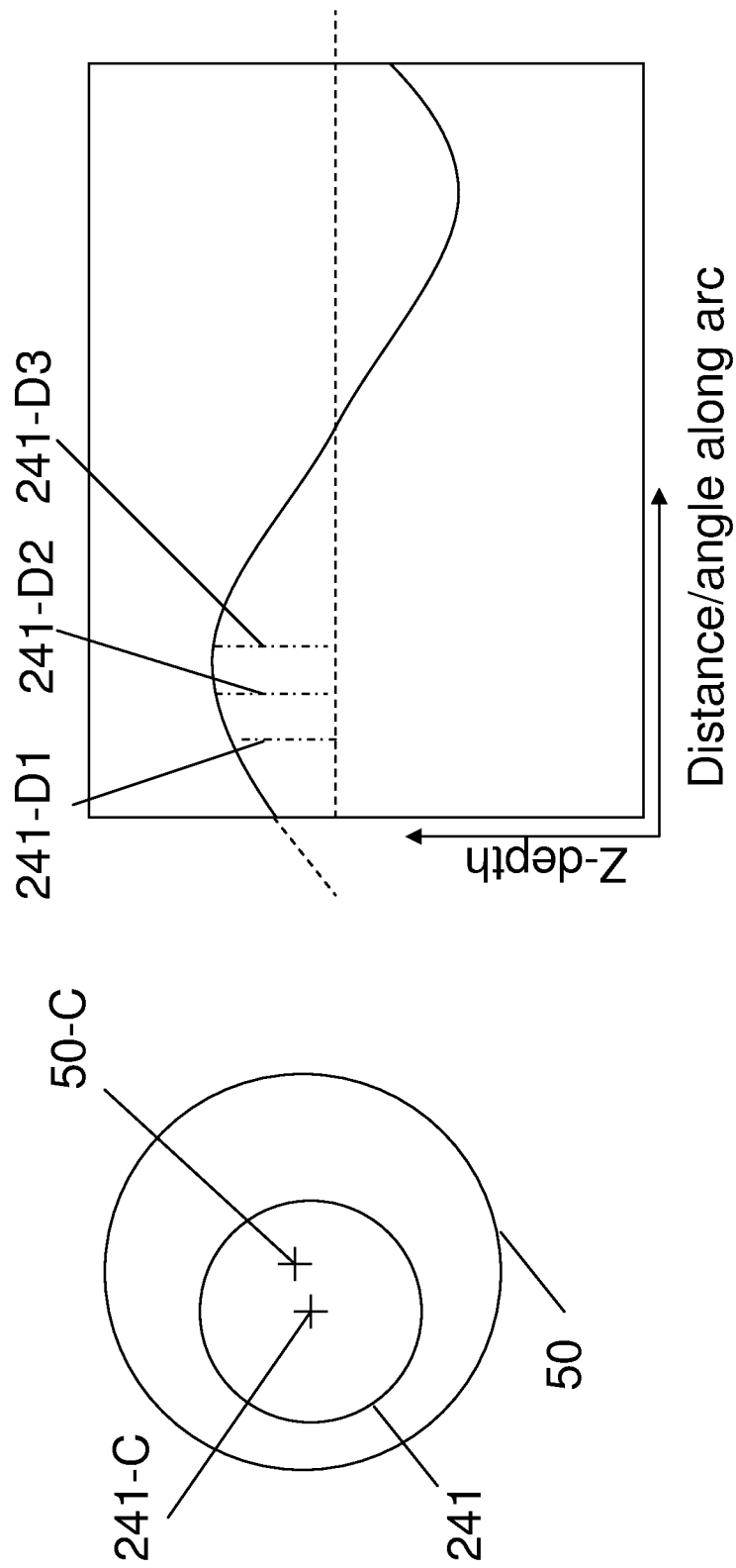

FIG. 4D illustrates how the target region parameters can be determined in step 140 based on the first and second scan data. In the left panel a circular scanning arc 241 is shown with its center 241-C offset from a center 50-C of the surgical target region, which is the lens 50 in this case. As described in the introduction, this or analogous situations can occur when the patient interface 210 is docked with its center off the center of the surgical target region.

In such situations, the surgical optical system may be operated in a way that compensates for this offset by, e.g., aligning the center of the target pattern 40 with the center of the lens 50-C. As discussed above, in various embodiments the center of the target pattern 40 coincides with the shared center of the first and second scanning arcs 241-C and 242-C. Thus, this task of aligning the centers translates to determining the offset of the center of, e.g., the first arc 241-C from the target center 50-C. Once this offset is determined, the center of the target pattern 40 can be shifted by this offset to align it properly with the lens-center 50-C. Subsequently, a surgical pattern can be defined using the properly centered target pattern 40 and the surgical laser beam can be applied according to the surgical pattern.

As described below, this adjustment may be based not only on the center of the surgical target region, but on various characteristic features of the surgical target region, such as a characteristic feature, a spot coloration, an irregular feature, a blood vessel, etc.

One method to facilitate such an adjusting is to extract first and second scan characteristics from the first and second scan data. Examples of these scan characteristics include a first amplitude and a first phase of the first scan data; and a second amplitude and a second phase of the second scan data.

As shown in the right panel of FIG. 4D, when the first loop 241 is an offset circle or ellipse on the target surface, the first scan, or depth, data 241-D1, . . . 241-Dn of the first arc-points 241-P1, . . . 241-Pn form a section of a sinusoidal curve. In general, this curve can be a function which can be represented by a Fourier sum of harmonics. If the scanning circle 241 is perfectly centered at the center of the target region, i.e. 241-C coincides with 50-C, then the first scan, or depth data will be a constant function.

If the first arc is a full circle, then the sinusoidal curve can have a full period of a sinusoidal. Typically, the scans do not start at the maxima or minima of the sinusoidal, thus the first scan, or depth, data, when plotted as a function of a distance along the scanning arc 241, take the shape of a sinusoidal starting with a phase shift.

Figure 4E:
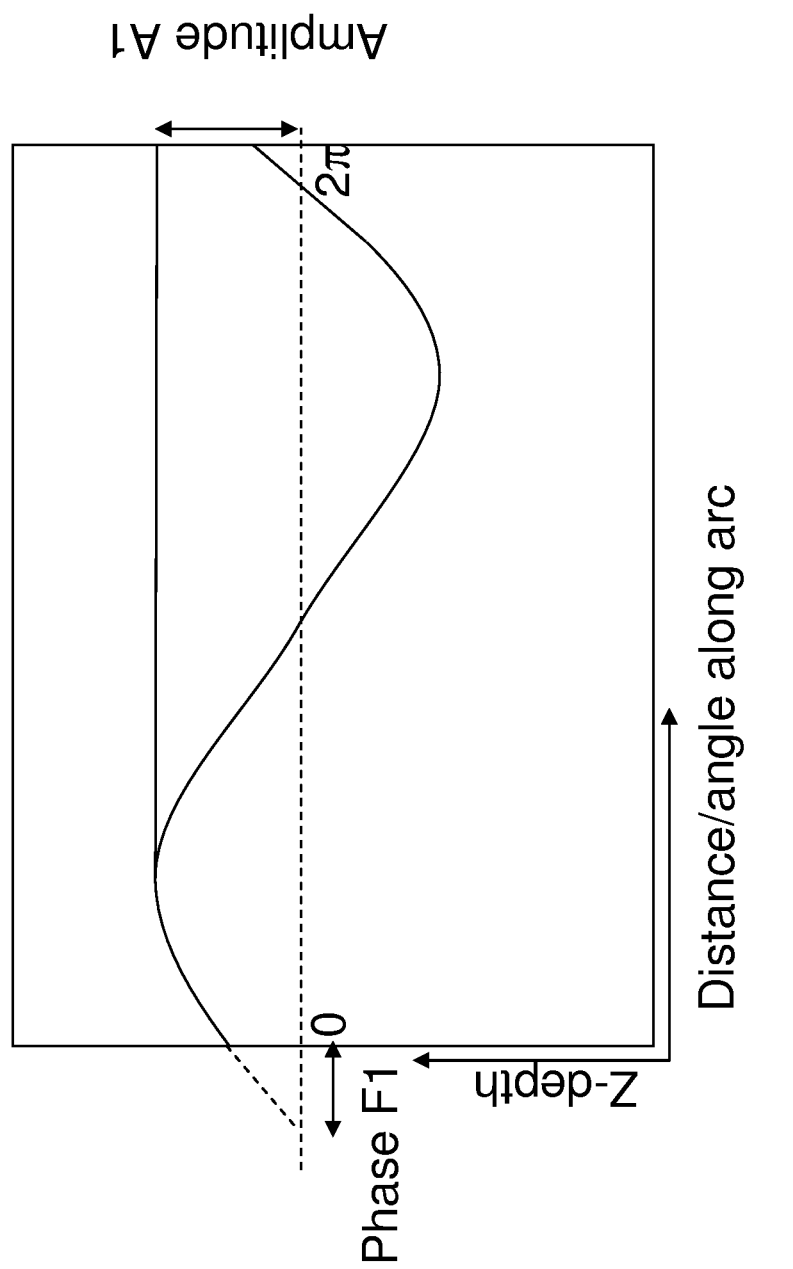

FIG. 4E illustrates that in such a case the first scan characteristics can be e.g. a phase F1 and an amplitude A1 of the sinusoidal of the first scan, or depth, data 241-D1, . . . , 241-Dn. These scan characteristics can be determined by fitting a sinusoidal function to the first scan, or depth, data, and treating the adjustable phase and amplitude of the sinusoidal as fitting parameters. Similarly, a second scan characteristics of a second amplitude A2 and second phase F2 can be extracted from fitting a sinusoidal to the second scan, or depth, data 242-D1, . . . 241-Dn.

In general, if the center of the scanning loop, and thus typically the center of the target pattern 40, coincides with the center of the lens 50, the scan data 241-D1, . . . 241-Dn are a constant, translating to a zero amplitude for the sinusoidal. The more offset the center of the scanning loop 241-C from the center of the lens 50, the larger the amplitude A1. Therefore, the amplitude A1 can characterize how far offset the center of the scanning loop 241-C and thus the target pattern 40 is relative to the center 50-C of the target region. The phase F1 may characterize which direction the shared center of the scanning circle 241-C and the target pattern 40 is offset from the center 50-C of the target region.

Such phase and amplitude scan characteristics can be extracted if the scanning arc 241 is not a circle, but an ellipse, or even an open arc. In the case when the scan data can be fitted not with a single sinusoidal, but with the sum of several, e.g. m, Fourier harmonics, the amplitudes A1, . . . Am and phases F1, . . . Fm of each of these Fourier harmonics can be extracted by standard fitting procedures. One or more of these amplitudes A1, . . . Am and phases F1, . . . Fm, or a subset of these amplitudes and phases can be used as scan characteristics.

Also, in some implementations, the scan characteristics can be a large variety of other characteristics, which are helpful for the eventual adjusting of center of the target pattern 40. Such scan characteristics can be the depth values at specific scan points themselves, gradients of the depth data points, triangulation related data, various moments of the fitted sinusoidal, or a characteristic of the higher harmonics. In some implementations the first and second scan data can exhibit a maximum and a minimum, and the scan characteristics can be related to these minima and maxima. The scan characteristics can be a suitable parameter or data, which can be used for the shifting of the target pattern 40.

Figure 5A:
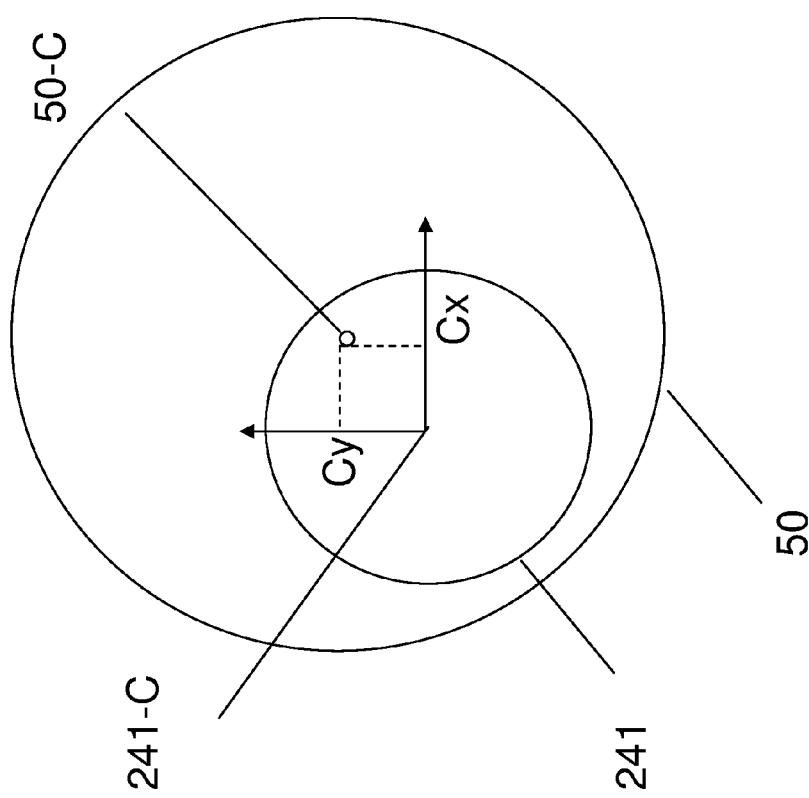
FIGS. 5A-B illustrate an adjusting of a surgical position parameter.

FIG. 5A illustrates that the determining the target region parameters step 140 may include determining a position parameter of a center of the target region 50-C based on the first amplitude A1, the first phase F1, the second amplitude A2 and the second phase F2. E.g. a computer controller can establish a coordinate system centered at the shared center 241-C of the scanning loop 241 and the target pattern 40. Using the first and second amplitudes A1, A2 and phases F1, F2, the $C_x$ and $C_y$ coordinates of the center of the target region 50-C can be determined relative to this coordinate system. These $C_x$ and $C_y$ coordinates are the sought after offset, or target region parameters, by which the center of the target pattern 40-C is to be shifted to align with the center of the target region, such as the lens 50-C.

In detail, this determining of the target region parameters step can be stated in general as:

$$TRj = TRj(Ai, Fi) \quad (1)$$

where TRj denote the target region parameters TR1 and TR2, Ai denote the amplitudes and Fi denote the phases, which are specific examples of the scan characteristics. In the specific case above, when the target region parameters TRi are the Cartesian coordinates $C_x$ and $C_y$ of the target region center within the reference frame of the target pattern 40, the above Eq. (1) reads:

$$C_x = C_x(A1, A2, F1, F2)$$

$$C_y = C_y(A1, A2, F1, F2) \quad (2)$$

In some implementations, only one scanning circle or loop may be sufficient to determine center coordinates $C_x$ and $C_y$:

$$C_x = C_x(A1, F1)$$

$$C_y = C_y(A1, F1) \quad (3)$$

In some other embodiments, the target region parameters TR1 and TR2 are the direction and the magnitude of the offset of the target center 50-C relative to the scan loop center 241-C, expressed e.g. in radial coordinates, which can also be determined from the phase F1, F2 and the amplitude A1, A2 scan characteristics.

In some implementations, the determining of the target region parameters step 140 can include determining a radius of curvature R parameter of the target region based on the first amplitude, first phase, second amplitude and second phase. An example can be the determination of a radius of curvature R of a cornea 220 or a lens 50. This radius of curvature R can be used in the determination of the offset of the target center 50-C from the shared center of the scan loop 241-C and target pattern 40-C:

$$C_x = C_x(A1, F1, R(A1, F1))$$

$$C_y = C_y(A1, F1, R(A1, F1)) \quad (4)$$

The sinusoidal behavior of the first scan, or depth data 241-D1, ... 241-Dn may have more than one origin. The above discussed offset of the target pattern center 40-C and the target region center 50-C is one primary origin. However, other factors can also contribute. These factors include a possible tilt of the optical axis of the eye, and a deviation from a purely spherical shape, such as the target region having an ellipsoidal shape.

These cases can be captured by the general terminology of shape parameters SPi, orientation parameters OPi and position parameters PPi. The radius of a spherical target R is a simple example of a shape parameter SP. Ellipsoidal targets can be characterized by three shape parameters SP1, SP2, and SP3, the length of their three axes a, b, and c. Obviously, the more complex shape the target has, the more shape parameters are required for its satisfactory characterization.

Completely spherical targets do not have orientation parameters OPi since all directions are equivalent because of their inherent spherical symmetry. But the orientation of all targets not possessing such complete spherical symmetry can be captured through orientation parameters OPi. Examples include spherical targets, having a distinguishing region, such as the pupil 10 on an (approximately) spherical eye. Other examples include ellipsoidal targets, where e.g. the components of the vectors, characterizing the orientation of the main axes, are examples of orientation parameters.

Of special interest is the lens 50, which to a good approximation has an ellipsoidal shape with two main axes, a and c, as the lens retained its rotational symmetry around one symmetry axis and thus the third axis b is equal to a. Thus, a and c are examples of the shape parameters SP1 and SP2 of the lens 50. The two components of the unit vector, describing the direction of the axis of rotational symmetry, also called the tilt vector, are examples of a set of orientation parameters OPi of the lens 50.

Finally, the coordinates Ci of the center of the lens 50-C are examples of the position parameters PPi. The position parameters PPi, the orientation parameters OPi and the shape parameters SPi together are a general list of target region parameters TRi.

In a general formulation, all these target region parameters TRi are extracted from the scan characteristics, such as the amplitudes Ai and phases Fi. In a formulation alternative to Eq. (4), these relations can be captured as:

$$PPj = PPj(Ai, Fi)$$

$$SPj = SPj(Ai, Fi)$$

$$OPj = OPj(Ai, Fi) \quad (5)$$

While the formulation of Eq. (4) indicated that the shape parameters SPi are determined as an intermediate step of the method, the formulation of Eq. (5) emphasizes that even the shape parameters SPj are determined from the scan characteristics. It is noted that indexing the target region parameters TRj differently from the scan characteristics Ai and Fi indicates that in general the number of TRj parameters can differ from the number of scan characteristics Ai and Fi. Typical embodiments extract a large enough number of scan characteristics Ai and Fi to be sufficient to determine all the necessary target region parameters TRj.

In some embodiments, a high fidelity determination of the target region parameters TRj can include supplementing the scan characteristics Ai and Fi with some of the scan data, such as the direct depth data 241-D1, ... 241Dn as well.

Some implementations of the method 100 use two scanning loops 241 and 242. Such a method will be demonstrated on the example of the lens 50. Approximating the lens anterior surface with a spherical one, having only one shape parameter SH1=R and formulating the method for the two position parameters in the XY plane PP1=Cx and PP2=Cy, the above two approaches are represented by the equations:

$$C_x = C_x(A1, A2, F1, F2, R(Ai, Fi))$$

$$C_y = C_y(A1, A2, F1, F2, R(Ai, Fi)) \quad (4')$$

and $$C_x = C_x(A1, A2, F1, F2)$$

$$C_y = C_y(A1, A2, F1, F2)$$

$$R = R(A1, A2, F1, F2) \quad (5')$$

These equations also demonstrate that extracting and using more scan characteristics than minimally necessary for determining the target region parameters TRj, in the present example 4 instead of the minimally necessary 3, can be an avenue to increase the fidelity of the eventual position parameters PPj.

Figure 5B:
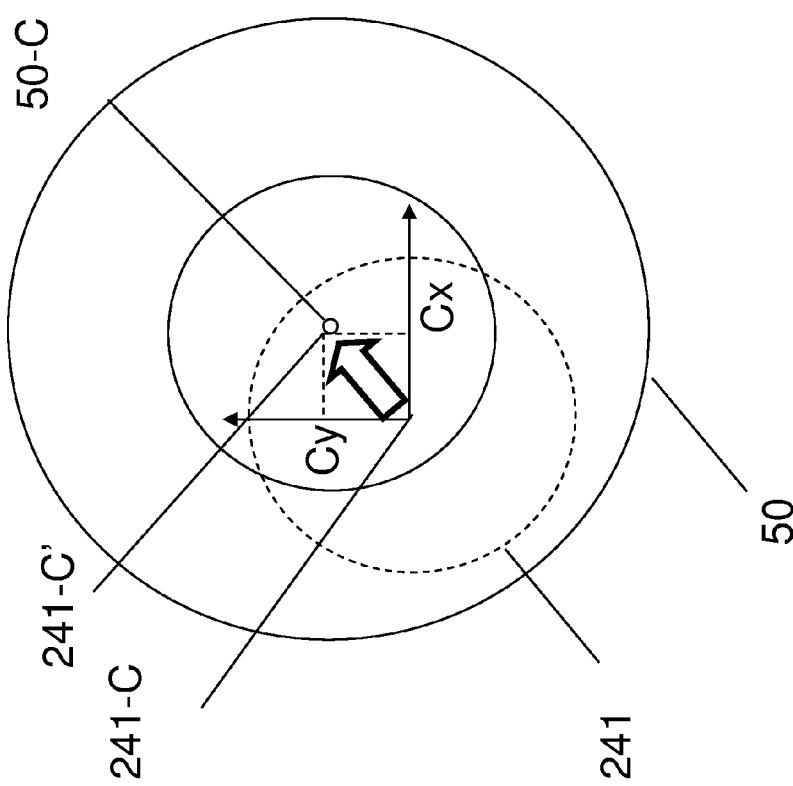

FIG. 5B illustrates that the determining of the target region parameters TRj step 140 may include determining a position parameter update, related to a position of the target region and a reference point. In the illustrated example, the reference point is the shared center of the scan loop 241 and target pattern 40, the position related to the target region is the center of the target region 50-C, and the position parameter update is the shift, or offset vector ($C_x$, $C_y$) by which the center of the target pattern 40 has to be shifted to overlap with the center of the target region 50-C.

As mentioned above, this shift vector can be given in a wide variety of forms including radial coordinates, indicating an angle of the shift and length of shift.

Step 140 may include shifting the center of the target pattern 40-C with the just-determined shift vector ($C_x$, $C_y$), so that the center of the target pattern 40-C overlaps the center of the target region 50-C.

The step 150 of adjusting the surgical position parameters may include adjusting a position parameter of a surgical pattern center to align the surgical pattern center with a center of the target region.

In some embodiments, the surgical pattern can be centered to the center of the target pattern 40. In these embodiments, step 150 can be carried out by shifting the shared center of the surgical pattern and the target pattern from its initial position by the shift vector, or position parameter update, determined in step 140.

In some other embodiments, first the target pattern can be shifted, followed by the shifting the surgical pattern.

As discussed above, this shift can be a single, integrated shift, or it can be a two step shift, where the first step may be performed either by practicing the guiding method 100 or by a manual or partially automated shift to center the target pattern 40 and the surgical pattern to an easily identifiable eye structure, such as the pupil 10. This shift can be followed by the second shift, moving the center of the target and surgical patterns to the center of the true target region, e.g. the lens 50.

In contrast to existing methods, implementations of the guiding method 100 can provide such a high accuracy determination of the position update, or shift vector, that typically the guiding method 100 can be performed only once, and the resulting position update, or shift vector aligns the surgical pattern with the surgical target region with a high accuracy. Therefore, in some implementations of the guiding method 100, the steps of the method can be performed only once to yield a satisfactory result.

This is to be contrasted with the limited accuracy of the existing methods where the steps of the method have to be performed iteratively and repeatedly, bringing the center of the target pattern closer and closer to the target region.

This high precision of the present guiding method 100 is particularly advantageous in all applications where time is at a premium, such as in eye surgical applications. The fact that the method 100 can be performed only once to yield high accuracy results means that in some implementations the time from the starting of the first scanning step to the finishing of the determination of the surgical position parameters step can be no more than 100 milliseconds, 1,000 milliseconds and 10,000 milliseconds. Each of these characteristic times can have critical advantages in time-sensitive applications.

Figure 6A:
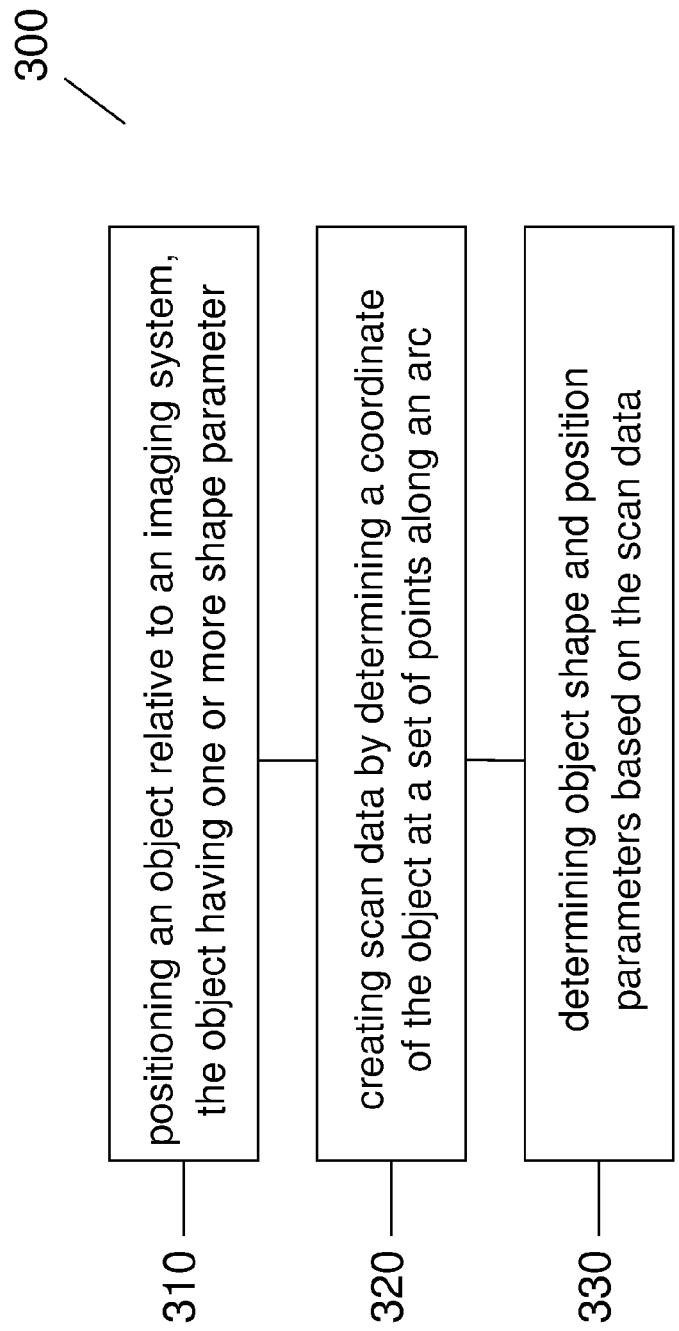
FIGS. 6A-B illustrate embodiments of imaging methods.

FIG. 6A illustrates that, while the guiding method 100 has been described in terms of an eye surgical application, the described concepts can be utilized in a large variety of imaging processes, not necessarily connected to ophthalmic applications. In general, the method 300 can be applied for imaging for invasive and non-invasive medical procedures. It can also be applied in a variety of manners for imaging for material processing, or for a non-invasive analysis of material fatigue, used from the airline industry to the nuclear industry, to name a few.

In any of these applications the imaging method 300 can include the following steps.

In step 310, positioning an object relative to an imaging system, wherein a shape of the object is describable in terms of one or more shape parameter and the orientation of the object is describable in terms of one or more orientation parameter.

In step 320, creating scan data by determining a coordinate of the object at a set of points along an arc.

In step 330, determining the object shape and orientation parameters and object position parameters based on the scan data 330.

The object can be a portion of a spherical surface layer, as e.g. shown in FIG. 4B, the determined object shape parameter $SP1$ can be a radius of the spherical surface layer R, and the object position parameters can be the XY coordinates of the center of the sphere, as e.g. expressed in Eqs. (1)-(5).

Or, the object can be an ellipsoid, the shape parameters $SPj$ can be the lengths of the three axes of the ellipsoid, the orientation parameters $OPj$ can be the angles of the unit vectors representing the direction of the main axes, and the position parameters $PPj$ can be the coordinates of the center of the ellipsoid.

While the method 300 was described with reference to the figures of the ophthalmic application, a very wide variety of imaging applications is envisioned here. An object which can reflect or alter light propagation in any way can be imaged by the imaging method 300. An object which can be characterized in terms of shape parameters can be imagined by the method 300. In some applications developed for studying material quality, the corrugation of material surfaces can be imaged. In some of these applications the shape parameter can be a typical feature size on the corrugated surface, or a typical unevenness of the grain or domain size of the material. In engineering applications where wear and fatigue of machine parts can be investigated, the shape of the machine part may be known from the design process, and the imaging method 300 may image the degree of deterioration or change of these known shape parameters, such as a narrowing of a diameter of a wire or a cross section of a beam.

Further, the imaging method 300 so far has been described in terms of closed objects, i.e. objects surrounded by a closed surface. In other embodiments, "open objects" can be imaged as well, which are surrounded by open surfaces. A class of open surfaces includes surfaces with boundaries or edges. Examples of open objects include portions of closed objects, e.g. a portion of a sphere or an ellipsoid, having a circular or an elliptic boundary or edge. Other examples include various surfaces, imaged for any engineering, quality control, material diagnostics and characterization purpose. A particular class of application of the imaging method 300 is for open objects which are not transparent. Many examples of such non-transparent open objects are imaged for a variety of reasons by the imaging method 300.

In many of these applications, the creating the scan data step 320 may provide sufficient data to determine the shape parameters, orientation parameters and position parameters of the imaged object, using the knowledge that the object can be characterized in terms of the particular shape parameters. In some other applications which image objects without an a priori knowledge of the object's shape, a processor may propose various shapes and analyze the scan data in terms of the proposed shapes. Using some fitting criteria, the processor may decide which proposed shape is the most appropriate for the imaged object and proceed with the determination of the object shape parameter and object position parameter.

In some embodiments the object can be an anterior lens surface layer of an eye, the object shape parameter a radius of the anterior lens surface layer, and the object position parameters the coordinates of a center of the anterior lens surface.

As above, the determining the object position parameters in step 330 can include imaging the object with at least one of an optical coherence tomography (OCT) method, an ultrasound-based method, a microscopic method and an interference based method.

The determining the object shape parameter and object position parameters step 330 can include creating auxiliary scan data by determining a coordinate of the object at an auxiliary set of points along an auxiliary arc. In some embodiments, this step can be practiced if the scan data along the original arc of step 320 is insufficient to determine the object's shape and position parameters. The arc of step 320 and the auxiliary arc of step 330 can be analogous to the arcs 241 and 242 of FIGS. 4A-C.

In some embodiments the object's coordinate is a Z coordinate of an object layer, and the arc is a portion of an intersection line where a scanning cylinder intersects the object layer.

The determining the object shape parameter in step 330 can include determining the Z coordinate of the object layer at the auxiliary set of points along an intersection line where an auxiliary cylinder intersects the object layer. In analogy to FIG. 4C, the scanning cylinder and the auxiliary cylinder can be essentially concentric, sharing a Z axis.

The determining the object shape parameter and object position parameter step 330 can include extracting an amplitude and a phase of the scan data, and determining a center of the object layer based on the extracted amplitude and phase.

In various implementations, the object position parameter can be a parameter of a center of the object layer or a perimeter of the object layer.

As above, because of the high efficiency of the method 300, in some implementations carrying out a single scan data creating step 320 can be sufficient, thus no additional scans are needed after the first scan, and possibly the first auxiliary scan. This is in contrast to existing systems, where the shape or position parameter may be determined iteratively, by repeating the scanning step 320.

Also, as above, the object position parameter and the object shape parameter can be carried out in an integrated manner.

Figure 6B:
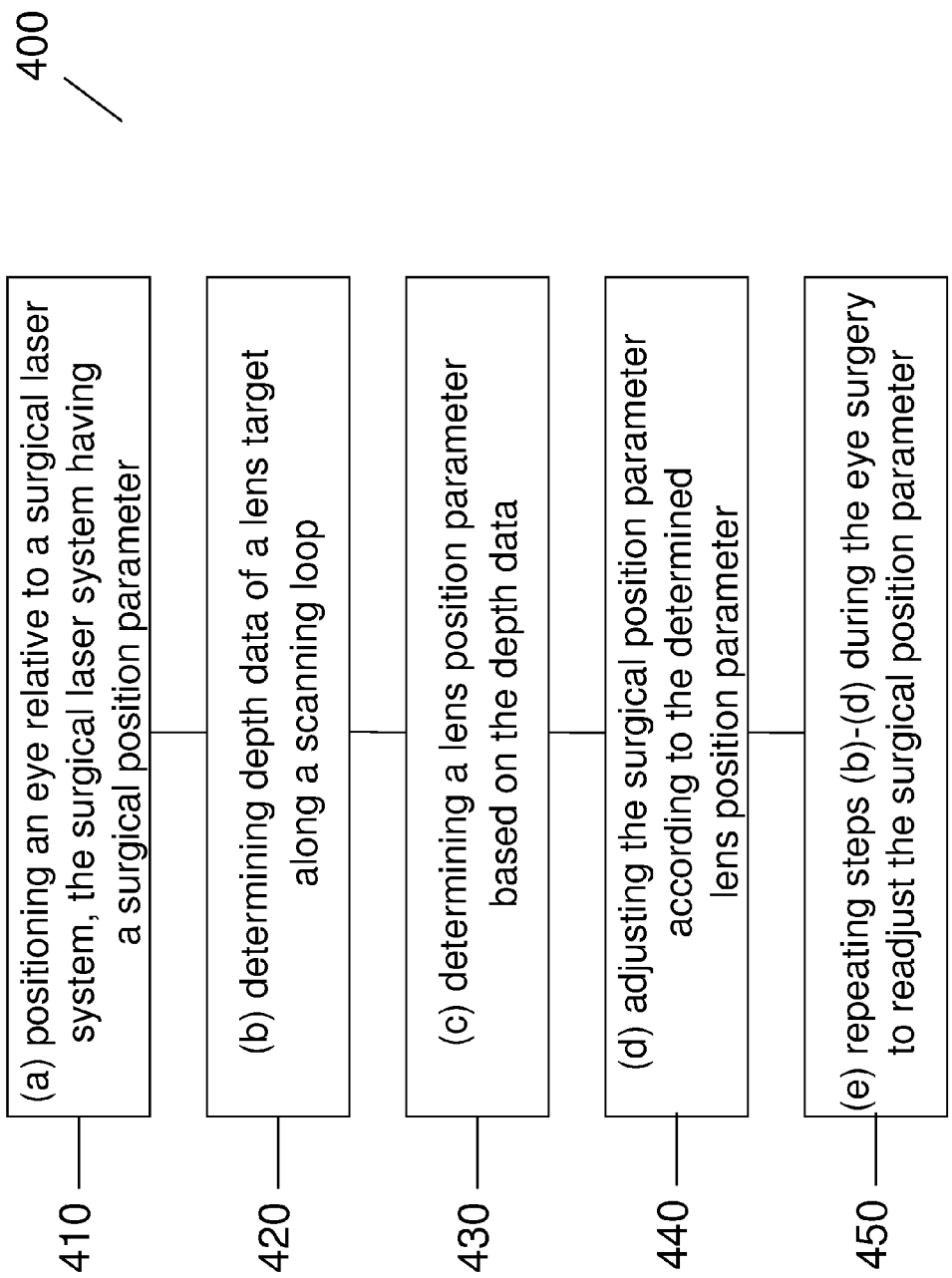

FIG. 6B illustrates an aspect of the above imaging methods 100 and 300. Since these methods are very efficient, they can deliver the target position data in a timely manner. This enables implementations to perform the imaging methods 100 or 300 repeatedly e.g. during a surgical procedure, to provide essentially real time or slightly delayed time position information. Then, if for whatever reason there was a change in the target region, such as the patient having moved his or her eye, the imaging system may be capable of determining updates to the target position parameter in a near real time manner, so that the surgical pattern can be shifted accordingly and the surgical laser can be applied according to the shifted surgical pattern. This (near) real time capability enhances the precision of the ophthalmic surgical procedure even more.

Such a (near) real time imaging and guiding method 400 for eye surgery can include the steps of:

(a) positioning an eye relative to a surgical laser system, the surgical laser system having a surgical position parameter and the eye having a lens—step 410;

(b) determining position data of a lens target region along a scanning arc—step 420;

(c) determining a lens position parameter based on the position data—step 430;

(d) adjusting the surgical position parameter according to the determined lens position parameter—step 440; and (e) repeating steps (b)-(d) during the eye surgery to readjust the surgical position parameter—step 450.

The method 400 can be used e.g. for surgeries where the lens target is one of an anterior lens surface, an anterior surface defined by a pupil, a lens target region and a posterior lens surface.

In analogy to FIGS. 4A-E, the determining the lens position parameters step 430 can include extracting an amplitude and a phase of the position data, and then determining a position parameter of a center of the lens target based on the amplitude and phase of the position data.

In some implementations, the adjusting a surgical position parameter step 440 can include adjusting a parameter of a surgical pattern center to align a surgical pattern in three dimensions with respect to a characteristic feature of the lens.

FIGS. 7-17 illustrate embodiments of a laser surgery system.

One important aspect of laser surgical procedures is precise control and aiming of a laser beam, e.g., the beam position and beam focusing. Laser surgery systems can be designed to include laser control and aiming tools to precisely target laser pulses to a particular target inside the tissue. In various nanosecond photodisruptive laser surgical systems, such as the Nd:YAG laser systems, the required level of targeting precision is relatively low. This is in part because the laser energy used is relatively high and thus the affected tissue area is also relatively large, often covering an impacted area with a dimension in the hundreds of microns. The time between laser pulses in such systems tend to be long and manual controlled targeting is feasible and is commonly used. One example of such manual targeting mechanisms is a biomicroscope to visualize the target tissue in combination with a secondary laser source used as an aiming beam. The surgeon manually moves the focus of a laser focusing lens, usually with a joystick control, which is parfocal (with or without an offset) with their image through the microscope, so that the surgical beam or aiming beam is in best focus on the intended target.

Such techniques designed for use with low repetition rate laser surgical systems may be difficult to use with high repetition rate lasers operating at thousands of shots per second and relatively low energy per pulse. In surgical operations with high repetition rate lasers, much higher precision may be required due to the small effects of each single laser pulse and much higher positioning speed may be required due to the need to deliver thousands of pulses to new treatment areas very quickly.

Examples of high repetition rate pulsed lasers for laser surgical systems include pulsed lasers at a pulse repetition rate of thousands of shots per second or higher with relatively low energy per pulse. Such lasers use relatively low energy per pulse to localize the tissue effect caused by laser-induced photodisruption, e.g., the impacted tissue area by photodisruption on the order of microns or tens of microns. This localized tissue effect can improve the precision of the laser surgery and can be desirable in certain surgical procedures such as laser eye surgery. In one example of such surgery, placement of many hundred, thousands or millions of contiguous, nearly contiguous or pulses separated by known distances, can be used to achieve certain desired surgical effects, such as tissue incisions, separations or fragmentation.

Various surgical procedures using high repetition rate photodisruptive laser surgical systems with shorter laser pulse durations may require high precision in positioning each pulse in the target tissue under surgery both in an absolute position with respect to a target location on the target tissue and a relative position with respect to preceding pulses. For example, in some cases, laser pulses may be required to be delivered next to each other with an accuracy of a few microns within the time between pulses, which can be on the order of microseconds. Because the time between two sequential pulses is short and the precision requirement for the pulse alignment is high, manual targeting as used in low repetition rate pulsed laser systems may be no longer adequate or feasible.

One technique to facilitate and control precise, high speed positioning requirement for delivery of laser pulses into the tissue is attaching a applanation plate made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. Contact lenses can be designed for various applications and targets inside the eye and other tissues, including ones that are disposable or reusable. The contact glass or applanation plate on the surface of the target tissue can be used as a reference plate relative to which laser pulses are focused through the adjustment of focusing elements within the laser delivery system. This use of a contact glass or applanation plate provides better control of the optical qualities of the tissue surface and thus allow laser pulses to be accurately placed at a high speed at a desired location (interaction point) in the target tissue relative to the applanation reference plate with little optical distortion of the laser pulses.

One way for implementing an applanation plate on an eye is to use the applanation plate to provide a positional reference for delivering the laser pulses into a target tissue in the eye. This use of the applanation plate as a positional reference can be based on the known desired location of laser pulse focus in the target with sufficient accuracy prior to firing the laser pulses and that the relative positions of the reference plate and the individual internal tissue target must remain constant during laser firing. In addition, this method can require the focusing of the laser pulse to the desired location to be predictable and repeatable between eyes or in different regions within the same eye. In practical systems, it can be difficult to use the applanation plate as a positional reference to precisely localize laser pulses intraocularly because the above conditions may not be met in practical systems.

For example, if the crystalline lens is the surgical target, the precise distance from the reference plate on the surface of the eye to the target tends to vary due to the presence of collapsible structures, such as the cornea itself, the anterior chamber, and the iris. Not only is their considerable variability in the distance between the applanated cornea and the lens between individual eyes, but there can also be variation within the same eye depending on the specific surgical and applanation technique used by the surgeon. In addition, there can be movement of the targeted lens tissue relative to the applanated surface during the firing of the thousands of laser pulses required for achieving the surgical effect, further complicating the accurate delivery of pulses. In addition, structure within the eye may move due to the build-up of photodisruptive byproducts, such as cavitation bubbles. For example, laser pulses delivered to the crystalline lens can cause the lens capsule to bulge forward, requiring adjustment to target this tissue for subsequent placement of laser pulses. Furthermore, it can be difficult to use computer models and simulations to predict, with sufficient accuracy, the actual location of target tissues after the applanation plate is removed and to adjust placement of laser pulses to achieve the desired localization without applanation in part because of the highly variable nature of applanation effects, which can depend on factors particular to the individual cornea or eye, and the specific surgical and applanation technique used by a surgeon.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption is a non-linear optical process in the tissue material and can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. In addition, it may be necessary to adjust the energy in each pulse to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses.

Thus, in surgical procedures in which non superficial structures are targeted, the use of a superficial applanation plate based on a positional reference provided by the applanation plate may be insufficient to achieve precise laser pulse localization in internal tissue targets. The use of the applanation plate as the reference for guiding laser delivery may require measurements of the thickness and plate position of the applanation plate with high accuracy because the deviation from nominal is directly translated into a depth precision error. High precision applanation lenses can be costly, especially for single use disposable applanation plates.

The techniques, apparatus and systems described in this document can be implemented in ways that provide a targeting mechanism to deliver short laser pulses through an applanation plate to a desired localization inside the eye with precision and at a high speed without requiring the known desired location of laser pulse focus in the target with sufficient accuracy prior to firing the laser pulses and without requiring that the relative positions of the reference plate and the individual internal tissue target remain constant during laser firing. As such, the present techniques, apparatus and systems can be used for various surgical procedures where physical conditions of the target tissue under surgery tend to vary and are difficult to control and the dimension of the applanation lens tends to vary from one lens to another. The present techniques, apparatus and systems may also be used for other surgical targets where distortion or movement of the surgical target relative to the surface of the structure is present or non-linear optical effects make precise targeting problematic. Examples for such surgical targets different from the eye include the heart, deeper tissue in the skin and others.

The present techniques, apparatus and systems can be implemented in ways that maintain the benefits provided by an applanation plate, including, for example, control of the surface shape and hydration, as well as reductions in optical distortion, while providing for the precise localization of photodisruption to internal structures of the applanated surface. This can be accomplished through the use of an integrated imaging device to localize the target tissue relative to the focusing optics of the delivery system. The exact type of imaging device and method can vary and may depend on the specific nature of the target and the required level of precision.

An applanation lens may be implemented with another mechanism to fix the eye to prevent translational and rotational movement of the eye. Examples of such fixation devices include the use of a suction ring. Such fixation mechanism can also lead to unwanted distortion or movement of the surgical target. The present techniques, apparatus and systems can be implemented to provide, for high repetition rate laser surgical systems that utilize an applanation plate and/or fixation means for non-superficial surgical targets, a targeting mechanism to provide intraoperative imaging to monitor such distortion and movement of the surgical target.

Specific examples of laser surgical techniques, apparatus and systems are described below to use an optical imaging module to capture images of a target tissue to obtain positioning information of the target tissue, e.g., before and during a surgical procedure. Such obtained positioning information can be used to control the positioning and focusing of the surgical laser beam in the target tissue to provide accurate control of the placement of the surgical laser pulses in high repetition rate laser systems. In one implementation, during a surgical procedure, the images obtained by the optical imaging module can be used to dynamically control the position and focus of the surgical laser beam. In addition, lower energy and shot laser pulses tend to be sensitive to optical distortions, such a laser surgical system can implement an applanation plate with a flat or curved interface attaching to the target tissue to provide a controlled and stable optical interface between the target tissue and the surgical laser system and to mitigate and control optical aberrations at the tissue surface.

Figure 7:
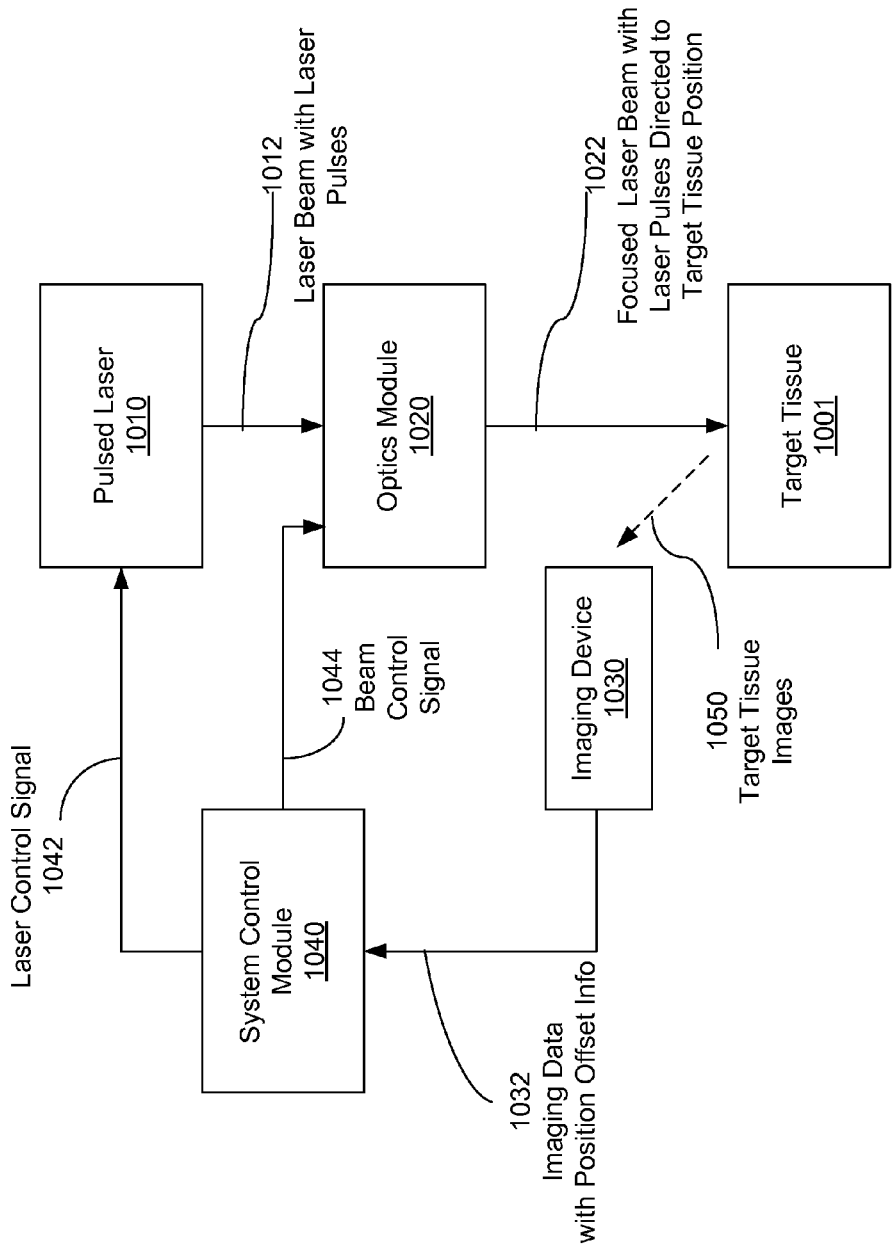
FIG. 7 shows an example of an imaging-guided laser surgical system in which an imaging module is provided to provide imaging of a target to the laser control.

As an example, FIG. 7 shows a laser surgical system based on optical imaging and applanation. This system includes a pulsed laser 1010 to produce a surgical laser beam 1012 of laser pulses, and an optics module 1020 to receive the surgical laser beam 1012 and to focus and direct the focused surgical laser beam 1022 onto a target tissue 1001, such as an eye, to cause photodisruption in the target tissue 1001. An applanation plate can be provided to be in contact with the target tissue 1001 to produce an interface for transmitting laser pulses to the target tissue 1001 and light coming from the target tissue 1001 through the interface. Notably, an optical imaging device 1030 is provided to capture light 1050 carrying target tissue images 1050 or imaging information from the target tissue 1001 to create an image of the target tissue 1001. The imaging signal 1032 from the imaging device 1030 is sent to a system control module 1040. The system control module 1040 operates to process the captured images from the image device 1030 and to control the optics module 1020 to adjust the position and focus of the surgical laser beam 1022 at the target tissue 1001 based on information from the captured images. The optics module 1020 can include one or more lenses and may further include one or more reflectors. A control actuator can be included in the optics module 1020 to adjust the focusing and the beam direction in response to a beam control signal 1044 from the system control module 1040. The control module 1040 can also control the pulsed laser 1010 via a laser control signal 1042.

The optical imaging device 1030 may be implemented to produce an optical imaging beam that is separate from the surgical laser beam 1022 to probe the target tissue 1001 and the returned light of the optical imaging beam is captured by the optical imaging device 1030 to obtain the images of the target tissue 1001. One example of such an optical imaging device 1030 is an optical coherence tomography (OCT) imaging module which uses two imaging beams, one probe beam directed to the target tissue 1001 thought the applanation plate and another reference beam in a reference optical path, to optically interfere with each other to obtain images of the target tissue 1001. In other implementations, the optical imaging device 1030 can use scattered or reflected light from the target tissue 1001 to capture images without sending a designated optical imaging beam to the target tissue 1001. For example, the imaging device 1030 can be a sensing array of sensing elements such as CCD or CMS sensors. For example, the images of photodisruption byproduct produced by the surgical laser beam 1022 may be captured by the optical imaging device 1030 for controlling the focusing and positioning of the surgical laser beam 1022. When the optical imaging device 1030 is designed to guide surgical laser beam alignment using the image of the photodisruption byproduct, the optical imaging device 1030 captures images of the photodisruption byproduct such as the laser-induced bubbles or cavities. The imaging device 1030 may also be an ultrasound imaging device to capture images based on acoustic images.

The system control module 1040 processes image data from the imaging device 1030 that includes the position offset information for the photodisruption byproduct from the target tissue position in the target tissue 1001. Based on the information obtained from the image, the beam control signal 1044 is generated to control the optics module 1020 which adjusts the laser beam 1022. A digital processing unit can be included in the system control module 1040 to perform various data processing for the laser alignment.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

The applanation plate in the present systems is provided to facilitate and control precise, high speed positioning requirement for delivery of laser pulses into the tissue. Such an applanation plate can be made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. A number of contact lenses have been designed for various applications and targets inside the eye and other tissues, including ones that are disposable or reusable. The contact glass or applanation plate on the surface of the target tissue is used as a reference plate relative to which laser pulses are focused through the adjustment of focusing elements within the laser delivery system relative. Inherent in such an approach are the additional benefits afforded by the contact glass or applanation plate described previously, including control of the optical qualities of the tissue surface. Accordingly, laser pulses can be accurately placed at a high speed at a desired location (interaction point) in the target tissue relative to the applanation reference plate with little optical distortion of the laser pulses.

The optical imaging device 1030 in FIG. 7 captures images of the target tissue 1001 via the applanation plate. The control module 1040 processes the captured images to extract position information from the captured images and uses the extracted position information as a position reference or guide to control the position and focus of the surgical laser beam 1022. This imaging-guided laser surgery can be implemented without relying on the applanation plate as a position reference because the position of the applanation plate tends to change due to various factors as discussed above. Hence, although the applanation plate provides a desired optical interface for the surgical laser beam to enter the target tissue and to capture images of the target tissue, it may be difficult to use the applanation plate as a position reference to align and control the position and focus of the surgical laser beam for accurate delivery of laser pulses. The imaging-guided control of the position and focus of the surgical laser beam based on the imaging device 1030 and the control module 1040 allows the images of the target tissue 1001, e.g., images of inner structures of an eye, to be used as position references, without using the applanation plate to provide a position reference.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. The energy of the laser pulses may be adjusted to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses. In this regard, the direct images obtained from the target issue by the imaging device 1030 can be used to monitor the actual position of the surgical laser beam 1022 which reflects the combined effects of nonlinear optical effects in the target tissue and provide position references for control of the beam position and beam focus.

The techniques, apparatus and systems described here can be used in combination of an applanation plate to provide control of the surface shape and hydration, to reduce optical distortion, and provide for precise localization of photodisruption to internal structures through the applanated surface. The imaging-guided control of the beam position and focus described here can be applied to surgical systems and procedures that use means other than applanation plates to fix the eye, including the use of a suction ring which can lead to distortion or movement of the surgical target.

The following sections first describe examples of techniques, apparatus and systems for automated imaging-guided laser surgery based on varying degrees of integration of imaging functions into the laser control part of the systems. An optical or other modality imaging module, such as an OCT imaging module, can be used to direct a probe light or other type of beam to capture images of a target tissue, e.g., structures inside an eye. A surgical laser beam of laser pulses such as femtosecond or picosecond laser pulses can be guided by position information in the captured images to control the focusing and positioning of the surgical laser beam during the surgery. Both the surgical laser beam and the probe light beam can be sequentially or simultaneously directed to the target tissue during the surgery so that the surgical laser beam can be controlled based on the captured images to ensure precision and accuracy of the surgery.

Such imaging-guided laser surgery can be used to provide accurate and precise focusing and positioning of the surgical laser beam during the surgery because the beam control is based on images of the target tissue following applanation or fixation of the target tissue, either just before or nearly simultaneously with delivery of the surgical pulses. Notably, certain parameters of the target tissue such as the eye measured before the surgery may change during the surgery due to various factor such as preparation of the target tissue (e.g., fixating the eye to an applanation lens) and the alternation of the target tissue by the surgical operations. Therefore, measured parameters of the target tissue prior to such factors and/or the surgery may no longer reflect the physical conditions of the target tissue during the surgery. The present imaging-guided laser surgery can mitigate technical issues in connection with such changes for focusing and positioning the surgical laser beam before and during the surgery.

The present imaging-guided laser surgery may be effectively used for accurate surgical operations inside a target tissue. For example, when performing laser surgery inside the eye, laser light is focused inside the eye to achieve optical breakdown of the targeted tissue and such optical interactions can change the internal structure of the eye. For example, the crystalline lens can change its position, shape, thickness and diameter during accommodation, not only between prior measurement and surgery but also during surgery. Attaching the eye to the surgical instrument by mechanical means can change the shape of the eye in a not well defined way and further, the change can vary during surgery due to various factors, e.g., patient movement. Attaching means include fixating the eye with a suction ring and applanating the eye with a flat or curved lens. These changes amount to as much as a few millimeters. Mechanically referencing and fixating the surface of the eye such as the anterior surface of the cornea or limbus does not work well when performing precision laser microsurgery inside the eye.

The post preparation or near simultaneous imaging in the present imaging-guided laser surgery can be used to establish three-dimensional positional references between the inside features of the eye and the surgical instrument in an environment where changes occur prior to and during surgery. The positional reference information provided by the imaging prior to applanation and/or fixation of the eye, or during the actual surgery reflects the effects of changes in the eye and thus provides an accurate guidance to focusing and positioning of the surgical laser beam. A system based on the present imaging-guided laser surgery can be configured to be simple in structure and cost efficient. For example, a portion of the optical components associated with guiding the surgical laser beam can be shared with optical components for guiding the probe light beam for imaging the target tissue to simplify the device structure and the optical alignment and calibration of the imaging and surgical light beams.

The imaging-guided laser surgical systems described below use the OCT imaging as an example of an imaging instrument and other non-OCT imaging devices may also be used to capture images for controlling the surgical lasers during the surgery. As illustrated in the examples below, integration of the imaging and surgical subsystems can be implemented to various degrees. In the simplest form without integrating hardware, the imaging and laser surgical subsystems are separated and can communicate to one another through interfaces. Such designs can provide flexibility in the designs of the two subsystems. Integration between the two subsystems, by some hardware components such as a patient interface, further expands the functionality by offering better registration of surgical area to the hardware components, more accurate calibration and may improve workflow. As the degree of integration between the two subsystems increases, such a system may be made increasingly cost-efficient and compact and system calibration will be further simplified and more stable over time. Examples for imaging-guided laser systems in FIGS. 8-16 are integrated at various degrees of integration.

One implementation of a present imaging-guided laser surgical system, for example, includes a surgical laser that produces a surgical laser beam of surgical laser pulses that cause surgical changes in a target tissue under surgery; a patient interface mount that engages a patient interface in contact with the target tissue to hold the target tissue in position; and a laser beam delivery module located between the surgical laser and the patient interface and configured to direct the surgical laser beam to the target tissue through the patient interface. This laser beam delivery module is operable to scan the surgical laser beam in the target tissue along a predetermined surgical pattern. This system also includes a laser control module that controls operation of the surgical laser and controls the laser beam delivery module to produce the predetermined surgical pattern and an OCT module positioned relative to the patient interface to have a known spatial relation with respect to the patient interface and the target issue fixed to the patient interface. The OCT module is configured to direct an optical probe beam to the target tissue and receive returned probe light of the optical probe beam from the target tissue to capture OCT images of the target tissue while the surgical laser beam is being directed to the target tissue to perform an surgical operation so that the optical probe beam and the surgical laser beam are simultaneously present in the target tissue. The OCT module is in communication with the laser control module to send information of the captured OCT images to the laser control module.

In addition, the laser control module in this particular system responds to the information of the captured OCT images to operate the laser beam delivery module in focusing and scanning of the surgical laser beam and adjusts the focusing and scanning of the surgical laser beam in the target tissue based on positioning information in the captured OCT images.

In some implementations, acquiring a complete image of a target tissue may not be necessary for registering the target to the surgical instrument and it may be sufficient to acquire a portion of the target tissue, e.g., a few points from the surgical region such as natural or artificial landmarks. For example, a rigid body has six degrees of freedom in 3D space and six independent points would be sufficient to define the rigid body. When the exact size of the surgical region is not known, additional points are needed to provide the positional reference. In this regard, several points can be used to determine the position and the curvature of the anterior and posterior surfaces, which are normally different, and the thickness and diameter of the crystalline lens of the human eye. Based on these data a body made up from two halves of ellipsoid bodies with given parameters can approximate and visualize a crystalline lens for practical purposes. In another implementation, information from the captured image may be combined with information from other sources, such as pre-operative measurements of lens thickness that are used as an input for the controller.

Figure 8:
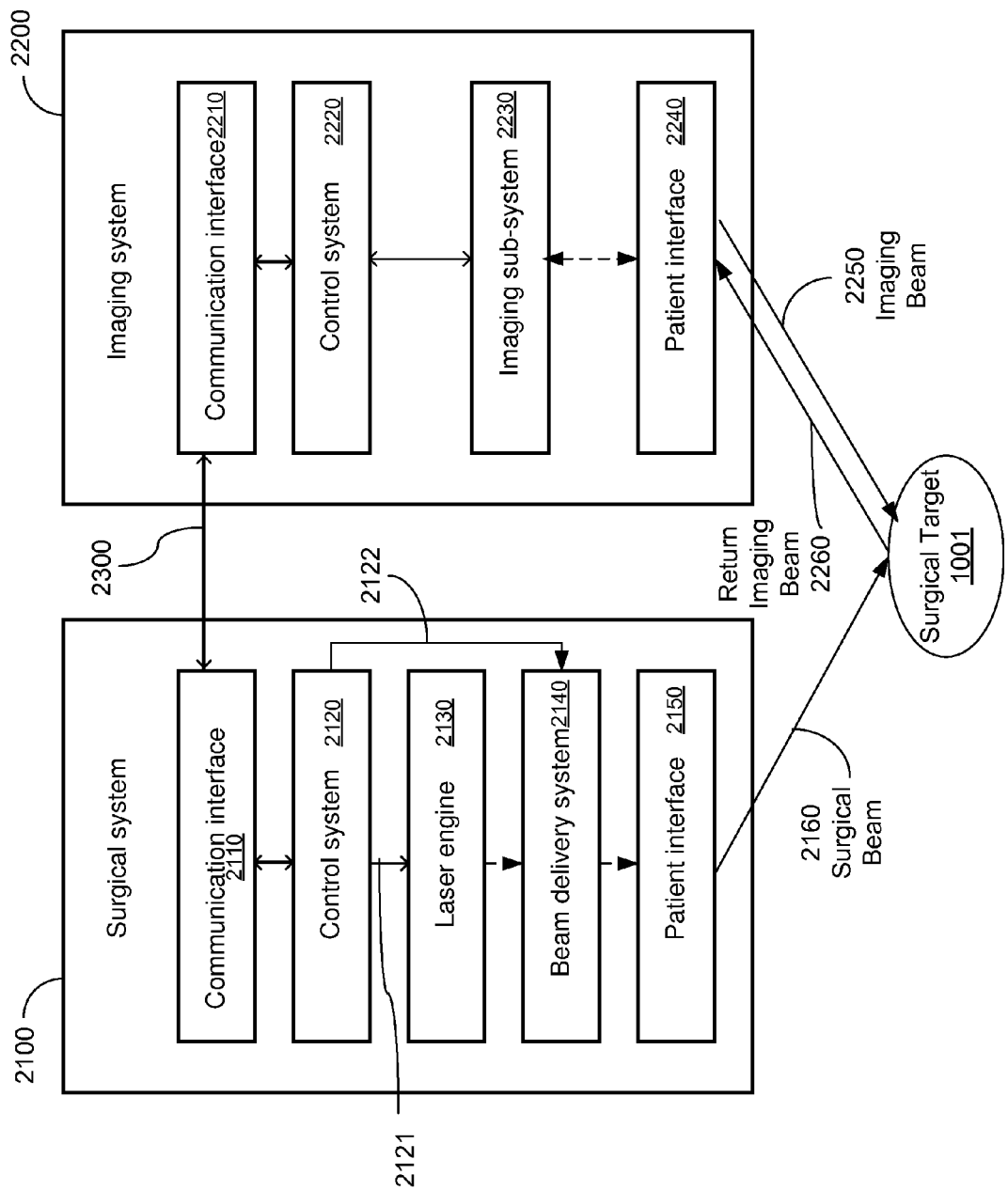
FIGS. 8-16 show examples of imaging-guided laser surgical systems with varying degrees of integration of a laser surgical system and an imaging system.

FIG. 8 shows one example of an imaging-guided laser surgical system with separated laser surgical system 2100 and imaging system 2200. The laser surgical system 2100 includes a laser engine 2130 with a surgical laser that produces a surgical laser beam 2160 of surgical laser pulses. A laser beam delivery module 2140 is provided to direct the surgical laser beam 2160 from the laser engine 2130 to the target tissue 1001 through a patient interface 2150 and is operable to scan the surgical laser beam 2160 in the target tissue 1001 along a predetermined surgical pattern. A laser control module 2120 is provided to control the operation of the surgical laser in the laser engine 2130 via a communication channel 2121 and controls the laser beam delivery module 2140 via a communication channel 2122 to produce the predetermined surgical pattern. A patient interface mount is provided to engage the patient interface 2150 in contact with the target tissue 1001 to hold the target tissue 1001 in position. The patient interface 2150 can be implemented to include a contact lens or applanation lens with a flat or curved surface to conformingly engage to the anterior surface of the eye and to hold the eye in position.

The imaging system 2200 in FIG. 8 can be an OCT module positioned relative to the patient interface 2150 of the surgical system 2100 to have a known spatial relation with respect to the patient interface 2150 and the target issue 1001 fixed to the patient interface 2150. This OCT module 2200 can be configured to have its own patient interface 2240 for interacting with the target tissue 1001. The imaging system 2200 includes an imaging control module 2220 and an imaging sub-system 2230. The sub-system 2230 includes a light source for generating imaging beam 2250 for imaging the target 1001 and an imaging beam delivery module to direct the optical probe beam or imaging beam 2250 to the target tissue 1001 and receive returned probe light 2260 of the optical imaging beam 2250 from the target tissue 1001 to capture OCT images of the target tissue 1001. Both the optical imaging beam 2250 and the surgical beam 2160 can be simultaneously directed to the target tissue 1001 to allow for sequential or simultaneous imaging and surgical operation.

As illustrated in FIG. 8, communication interfaces 2110 and 2210 are provided in both the laser surgical system 2100 and the imaging system 2200 to facilitate the communications between the laser control by the laser control module 2120 and imaging by the imaging system 2200 so that the OCT module 2200 can send information of the captured OCT images to the laser control module 2120. The laser control module 2120 in this system responds to the information of the captured OCT images to operate the laser beam delivery module 2140 in focusing and scanning of the surgical laser beam 2160 and dynamically adjusts the focusing and scanning of the surgical laser beam 2160 in the target tissue 1001 based on positioning information in the captured OCT images. The integration between the laser surgical system 2100 and the imaging system 2200 is mainly through communication between the communication interfaces 2110 and 2210 at the software level.

In this and other examples, various subsystems or devices may also be integrated. For example, certain diagnostic instruments such as wavefront aberrometers, corneal topography measuring devices may be provided in the system, or pre-operative information from these devices can be utilized to augment intra-operative imaging.

Figure 9:
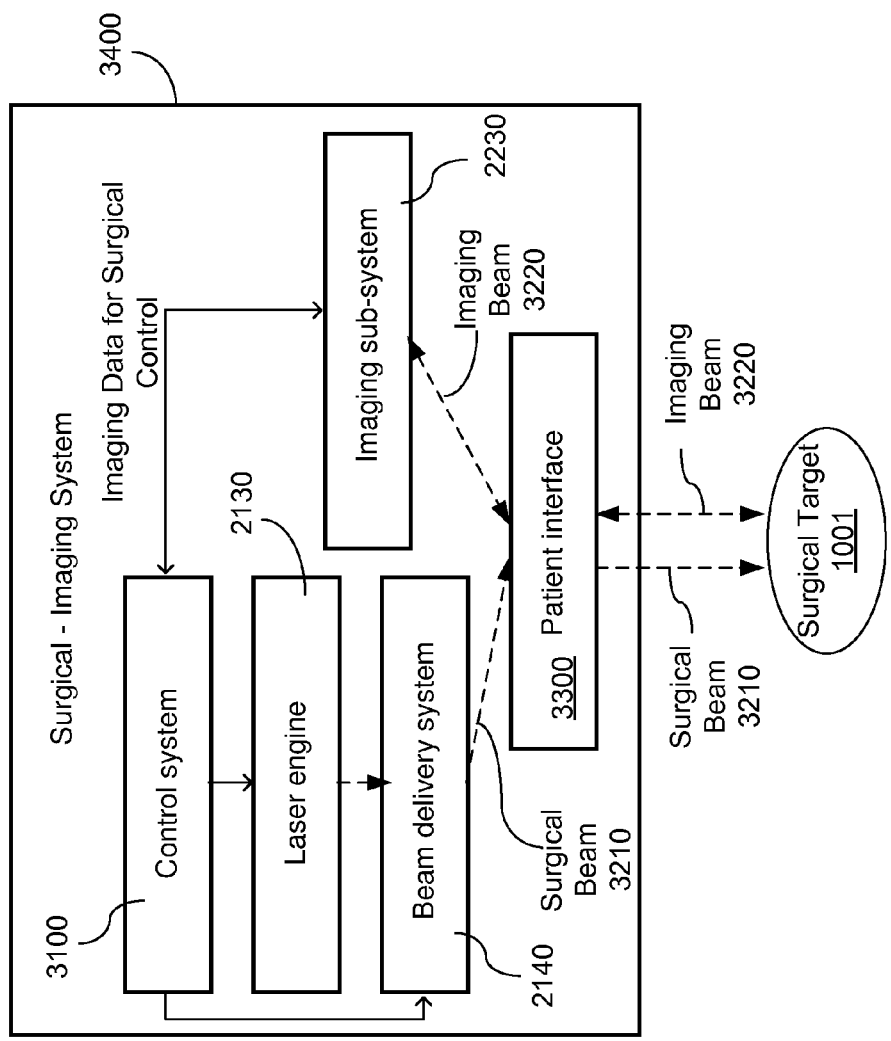

FIG. 9 shows an example of an imaging-guided laser surgical system with additional integration features. The imaging and surgical systems share a common patient interface 3300 which immobilizes target tissue 1001 (e.g., the eye) without having two separate patient interfaces as in FIG. 8. The surgical beam 3210 and the imaging beam 3220 are combined at the patient interface 3330 and are directed to the target 1001 by the common patient interface 3300. In addition, a common control module 3100 is provided to control both the imaging sub-system 2230 and the surgical part (the laser engine 2130 and the beam delivery system 2140). This increased integration between imaging and surgical parts allows accurate calibration of the two subsystems and the stability of the position of the patient and surgical volume. A common housing 3400 is provided to enclose both the surgical and imaging subsystems. When the two systems are not integrated into a common housing, the common patient interface 3300 can be part of either the imaging or the surgical subsystem.

Figure 10:
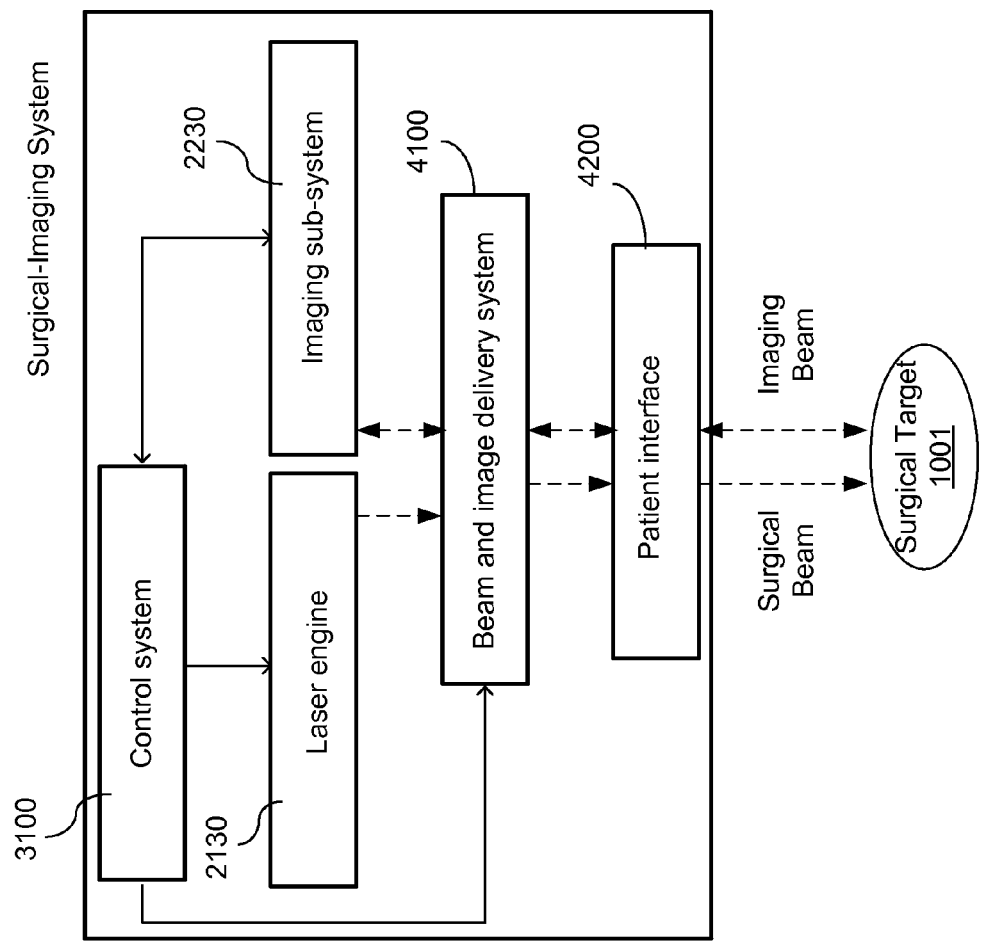

FIG. 10 shows an example of an imaging-guided laser surgical system where the laser surgical system and the imaging system share both a common beam delivery module 4100 and a common patient interface 4200. This integration further simplifies the system structure and system control operation.

In one implementation, the imaging system in the above and other examples can be an optical computed tomography (OCT) system and the laser surgical system is a femtosecond or picosecond laser based ophthalmic surgical system. In OCT, light from a low coherence, broadband light source such as a super luminescent diode is split into separate reference and signal beams. The signal beam is the imaging beam sent to the surgical target and the returned light of the imaging beam is collected and recombined coherently with the reference beam to form an interferometer. Scanning the signal beam perpendicularly to the optical axis of the optical train or the propagation direction of the light provides spatial resolution in the x-y direction while depth resolution comes from extracting differences between the path lengths of the reference arm and the returned signal beam in the signal arm of the interferometer. While the x-y scanner of different OCT implementations are essentially the same, comparing the path lengths and getting z-scan information can happen in different ways. In one implementation known as the time domain OCT, for example, the reference arm is continuously varied to change its path length while a photodetector detects interference modulation in the intensity of the recombined beam. In a different implementation, the reference arm is essentially static and the spectrum of the combined light is analyzed for interference. The Fourier transform of the spectrum of the combined beam provides spatial information on the scattering from the interior of the sample. This method is known as the spectral domain or Fourier OCT method. In a different implementation known as a frequency swept OCT (S. R. Chinn, et. al., Opt. Lett. 22, 1997), a narrowband light source is used with its frequency swept rapidly across a spectral range. Interference between the reference and signal arms is detected by a fast detector and dynamic signal analyzer. An external cavity tuned diode laser or frequency tuned of frequency domain mode-locked (FDML) laser developed for this purpose (R. Huber et. Al. Opt. Express, 13, 2005) (S. H. Yun, IEEE J. of Sel. Q. El. 3(4) p. 1087-1096, 1997) can be used in these examples as a light source. A femtosecond laser used as a light source in an OCT system can have sufficient bandwidth and can provide additional benefits of increased signal to noise ratios.

The OCT imaging device in the systems in this document can be used to perform various imaging functions. For example, the OCT can be used to suppress complex conjugates resulting from the optical configuration of the system or the presence of the applanation plate, capture OCT images of selected locations inside the target tissue to provide three-dimensional positioning information for controlling focusing and scanning of the surgical laser beam inside the target tissue, or capture OCT images of selected locations on the surface of the target tissue or on the applanation plate to provide positioning registration for controlling changes in orientation that occur with positional changes of the target, such as from upright to supine. The OCT can be calibrated by a positioning registration process based on placement of marks or markers in one positional orientation of the target that can then be detected by the OCT module when the target is in another positional orientation. In other implementations, the OCT imaging device can be used to produce a probe light beam that is polarized to optically gather the information on the internal structure of the eye. The laser beam and the probe light beam may be polarized in different polarizations. The OCT can include a polarization control mechanism that controls the probe light used for said optical tomography to polarize in one polarization when traveling toward the eye and in a different polarization when traveling away from the eye. The polarization control mechanism can include, e.g., a wave-plate or a Faraday rotator.

The system in FIG. 10 is shown as a spectral OCT configuration and can be configured to share the focusing optics part of the beam delivery module between the surgical and the imaging systems. The main requirements for the optics are related to the operating wavelength, image quality, resolution, distortion etc. The laser surgical system can be a femtosecond laser system with a high numerical aperture system designed to achieve diffraction limited focal spot sizes, e.g., about 2 to 3 micrometers. Various femtosecond ophthalmic surgical lasers can operate at various wavelengths such as wavelengths of around 1.05 micrometer. The operating wavelength of the imaging device can be selected to be close to the laser wavelength so that the optics is chromatically compensated for both wavelengths. Such a system may include a third optical channel, a visual observation channel such as a surgical microscope, to provide an additional imaging device to capture images of the target tissue. If the optical path for this third optical channel shares optics with the surgical laser beam and the light of the OCT imaging device, the shared optics can be configured with chromatic compensation in the visible spectral band for the third optical channel and the spectral bands for the surgical laser beam and the OCT imaging beam.

Figure 11:
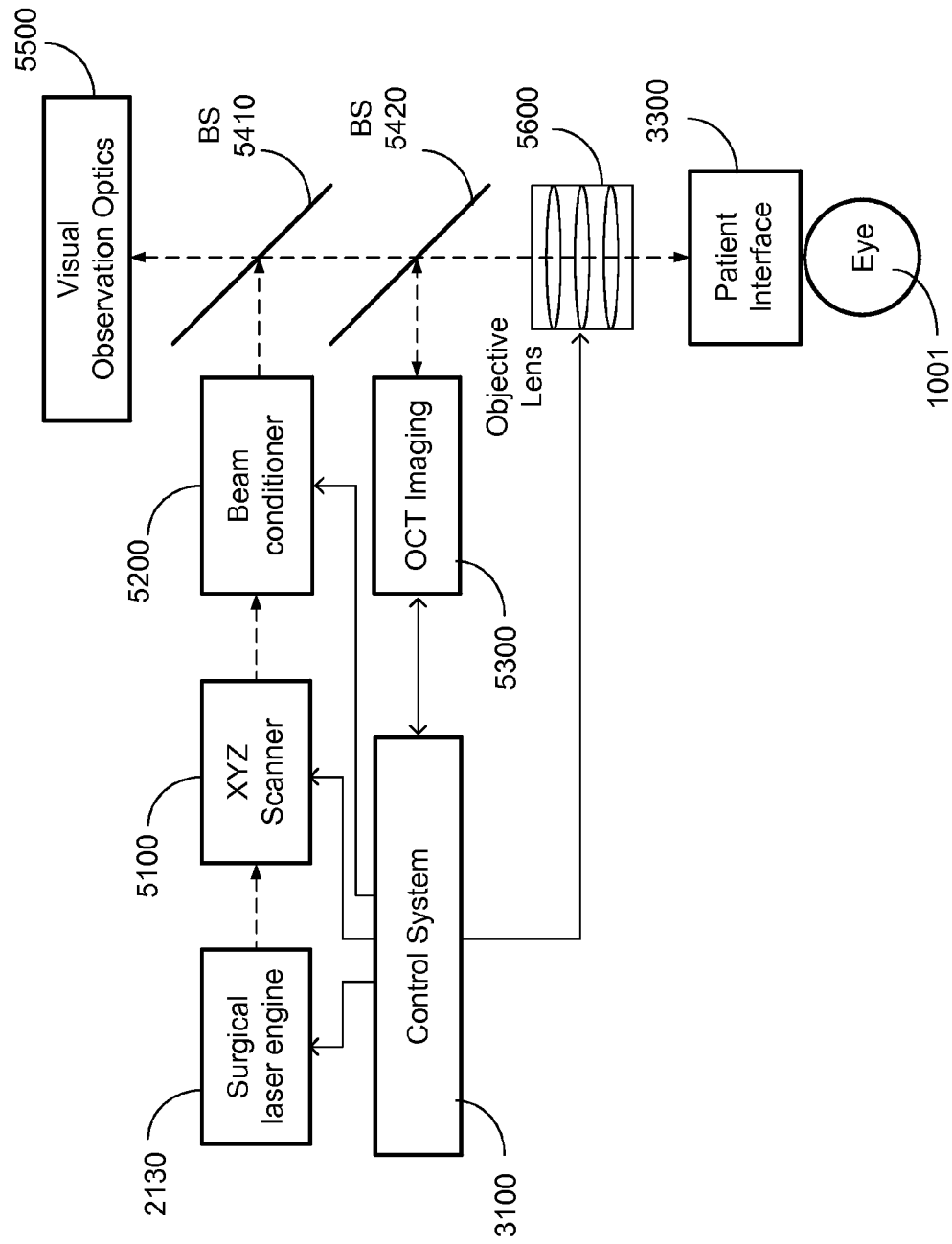

FIG. 11 shows a particular example of the design in FIG. 9 where the scanner 5100 for scanning the surgical laser beam and the beam conditioner 5200 for conditioning (collimating and focusing) the surgical laser beam are separate from the optics in the OCT imaging module 5300 for controlling the imaging beam for the OCT. The surgical and imaging systems share an objective lens 5600 module and the patient interface 3300. The objective lens 5600 directs and focuses both the surgical laser beam and the imaging beam to the patient interface 3300 and its focusing is controlled by the control module 3100. Two beam splitters 5410 and 5420 are provided to direct the surgical and imaging beams. The beam splitter 5420 is also used to direct the returned imaging beam back into the OCT imaging module 5300. Two beam splitters 5410 and 5420 also direct light from the target 1001 to a visual observation optics unit 5500 to provide direct view or image of the target 1001. The unit 5500 can be a lens imaging system for the surgeon to view the target 1001 or a camera to capture the image or video of the target 1001. Various beam splitters can be used, such as dichroic and polarization beam splitters, optical grating, holographic beam splitter or a combinations of these.

In some implementations, the optical components may be appropriately coated with antireflection coating for both the surgical and for the OCT wavelength to reduce glare from multiple surfaces of the optical beam path. Reflections would otherwise reduce the throughput of the system and reduce the signal to noise ratio by increasing background light in the OCT imaging unit. One way to reduce glare in the OCT is to rotate the polarization of the return light from the sample by wave-plate of Faraday isolator placed close to the target tissue and orient a polarizer in front of the OCT detector to preferentially detect light returned from the sample and suppress light scattered from the optical components.

In a laser surgical system, each of the surgical laser and the OCT system can have a beam scanner to cover the same surgical region in the target tissue. Hence, the beam scanning for the surgical laser beam and the beam scanning for the imaging beam can be integrated to share common scanning devices.

Figure 12:
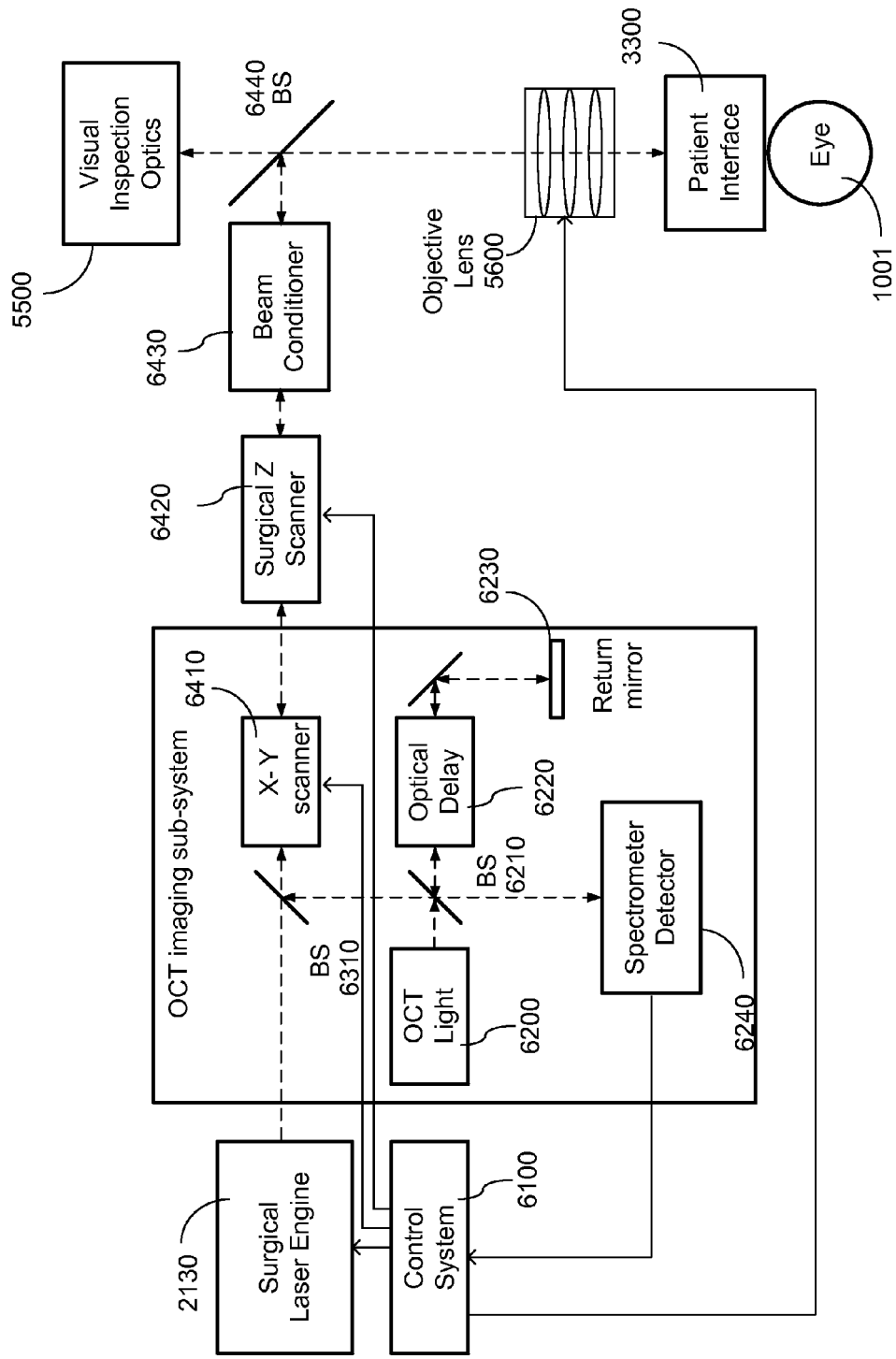

FIG. 12 shows an example of such a system in detail. In this implementation the x-y scanner 6410 and the z scanner 6420 are shared by both subsystems. A common control 6100 is provided to control the system operations for both surgical and imaging operations. The OCT sub-system includes an OCT light source 6200 that produce the imaging light that is split into an imaging beam and a reference beam by a beam splitter 6210. The imaging beam is combined with the surgical beam at the beam splitter 6310 to propagate along a common optical path leading to the target 1001. The scanners 6410 and 6420 and the beam conditioner 6430 are located downstream from the beam splitter 6310. A beam splitter 6440 is used to direct the imaging and surgical beams to the objective lens 5600 and the patient interface 3300.

In the OCT sub-system, the reference beam transmits through the beam splitter 6210 to an optical delay device 6220 and is reflected by a return mirror 6230. The returned imaging beam from the target 1001 is directed back to the beam splitter 6310 which reflects at least a portion of the returned imaging beam to the beam splitter 6210 where the reflected reference beam and the returned imaging beam overlap and interfere with each other. A spectrometer detector 6240 is used to detect the interference and to produce OCT images of the target 1001. The OCT image information is sent to the control system 6100 for controlling the surgical laser engine 2130, the scanners 6410 and 6420 and the objective lens 5600 to control the surgical laser beam. In one implementation, the optical delay device 6220 can be varied to change the optical delay to detect various depths in the target tissue 1001.

If the OCT system is a time domain system, the two subsystems use two different z-scanners because the two scanners operate in different ways. In this example, the z scanner of the surgical system operates by changing the divergence of the surgical beam in the beam conditioner unit without changing the path lengths of the beam in the surgical beam path. On the other hand, the time domain OCT scans the z-direction by physically changing the beam path by a variable delay or by moving the position of the reference beam return mirror. After calibration, the two z-scanners can be synchronized by the laser control module. The relationship between the two movements can be simplified to a linear or polynomial dependence, which the control module can handle or alternatively calibration points can define a look-up table to provide proper scaling. Spectral/Fourier domain and frequency swept source OCT devices have no z-scanner, the length of the reference arm is static. Besides reducing costs, cross calibration of the two systems will be relatively straightforward. There is no need to compensate for differences arising from image distortions in the focusing optics or from the differences of the scanners of the two systems since they are shared.

In practical implementations of the surgical systems, the focusing objective lens 5600 is slidably or movably mounted on a base and the weight of the objective lens is balanced to limit the force on the patient's eye. The patient interface 3300 can include an applanation lens attached to a patient interface mount. The patient interface mount is attached to a mounting unit, which holds the focusing objective lens. This mounting unit is designed to ensure a stable connection between the patient interface and the system in case of unavoidable movement of the patient and allows gentler docking of the patient interface onto the eye. Various implementations for the focusing objective lens can be used and one example is described in U.S. Pat. No. 5,336,215 to Hsueh. This presence of an adjustable focusing objective lens can change the optical path length of the optical probe light as part of the optical interferometer for the OCT sub-system. Movement of the objective lens 5600 and patient interface 3300 can change the path length differences between the reference beam and the imaging signal beam of the OCT in an uncontrolled way and this may degrade the OCT depth information detected by the OCT. This would happen not only in time-domain but also in spectral/Fourier domain and frequency-swept OCT systems.

Figure 13:
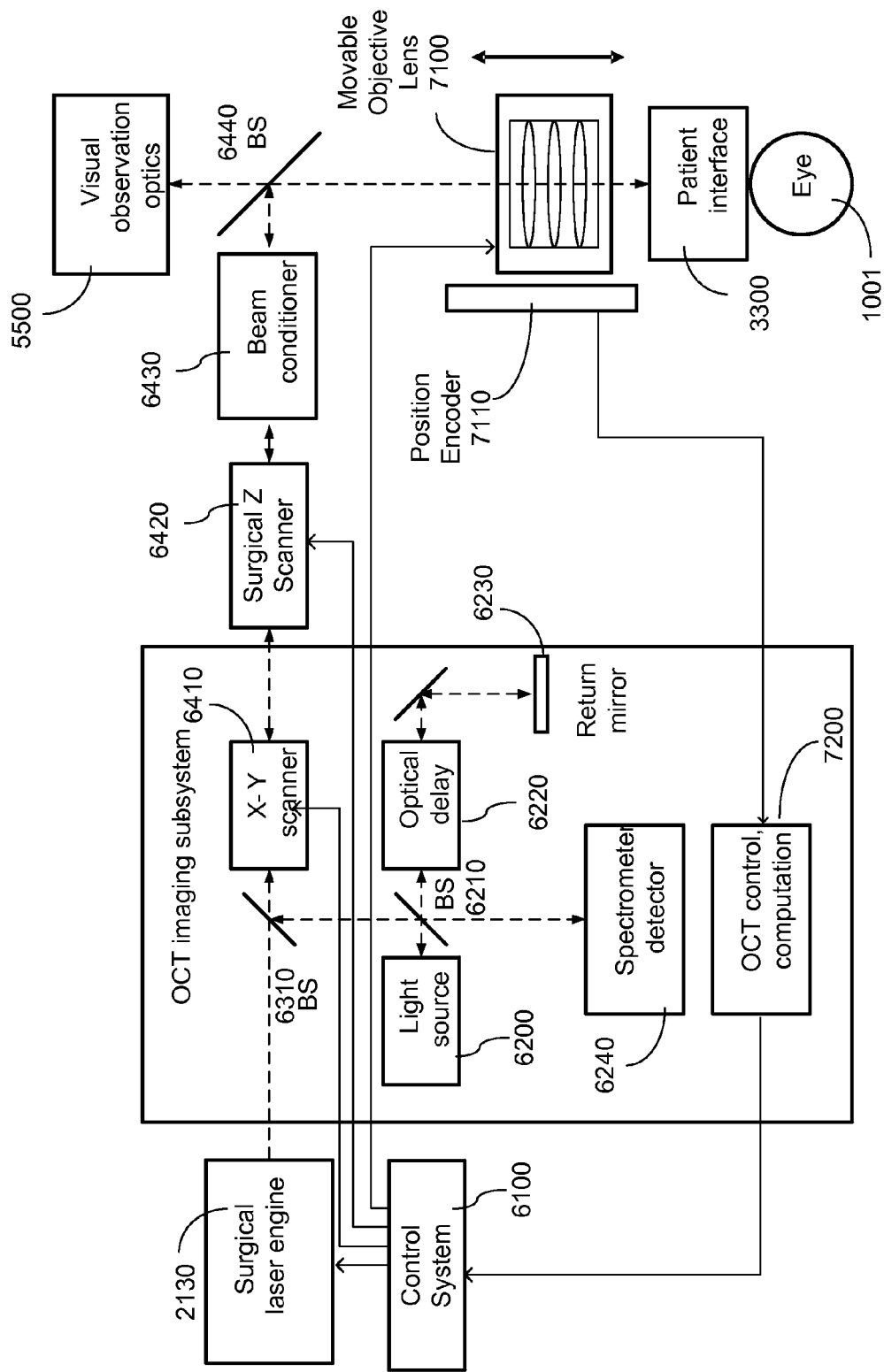
Figure 14:
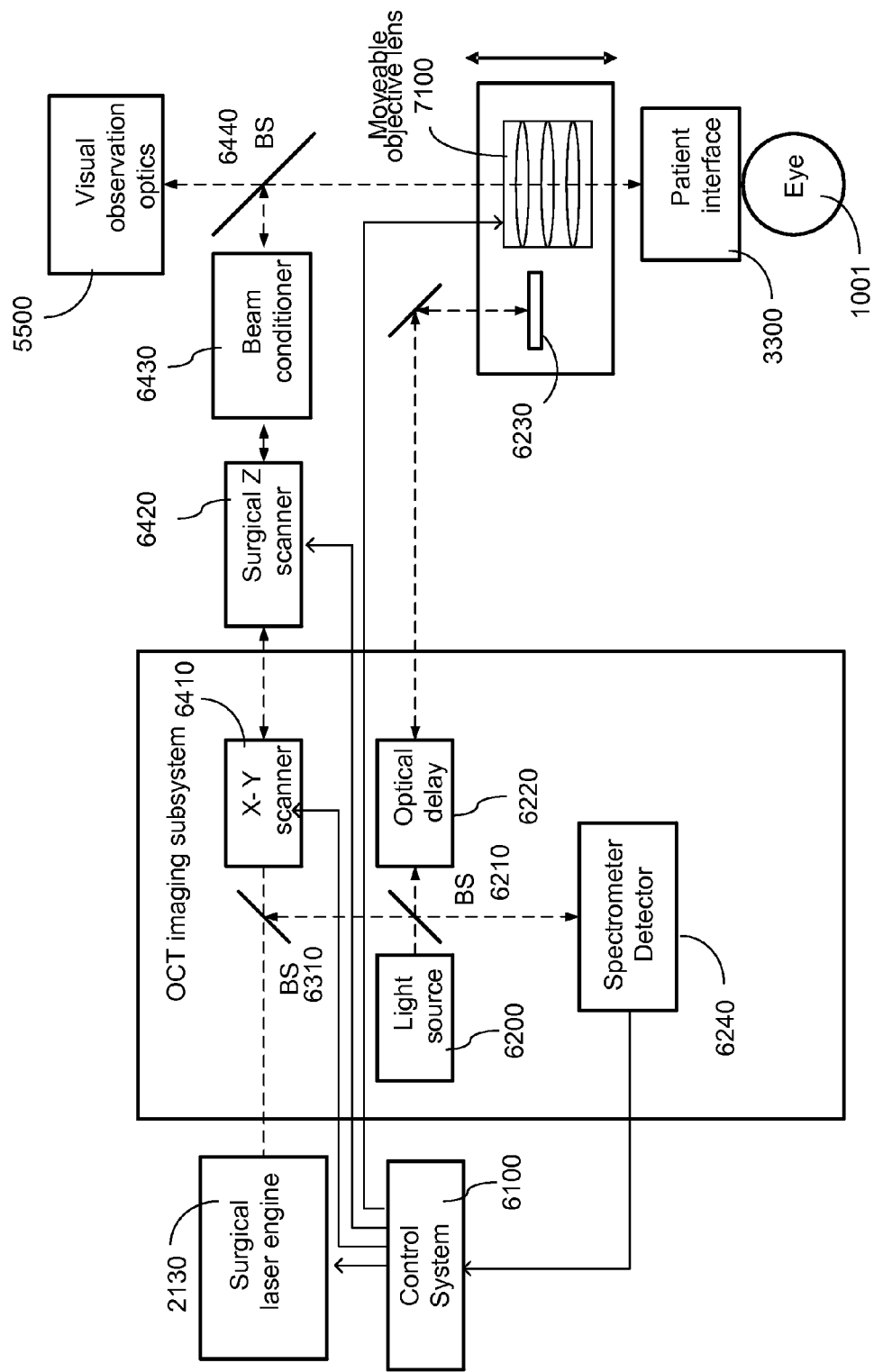

FIGS. 13-14 show exemplary imaging-guided laser surgical systems that address the technical issue associated with the adjustable focusing objective lens.

The system in FIG. 13 provides a position sensing device 7110 coupled to the movable focusing objective lens 7100 to measure the position of the objective lens 7100 on a slideable mount and communicates the measured position to a control module 7200 in the OCT system. The control system 6100 can control and move the position of the objective lens 7100 to adjust the optical path length traveled by the imaging signal beam for the OCT operation and the position of the lens 7100 is measured and monitored by the position encoder 7110 and direct fed to the OCT control 7200. The control module 7200 in the OCT system applies an algorithm, when assembling a 3D image in processing the OCT data, to compensate for differences between the reference arm and the signal arm of the interferometer inside the OCT caused by the movement of the focusing objective lens 7100 relative to the patient interface 3300. The proper amount of the change in the position of the lens 7100 computed by the OCT control module 7200 is sent to the control 6100 which controls the lens 7100 to change its position.

FIG. 14 shows another exemplary system where the return mirror 6230 in the reference arm of the interferometer of the OCT system or at least one part in an optical path length delay assembly of the OCT system is rigidly attached to the movable focusing objective lens 7100 so the signal arm and the reference arm undergo the same amount of change in the optical path length when the objective lens 7100 moves. As such, the movement of the objective lens 7100 on the slide is automatically compensated for pathlength differences in the OCT system without additional need for a computational compensation.

The above examples for imaging-guided laser surgical systems, the laser surgical system and the OCT system use different light sources. In an even more complete integration between the laser surgical system and the OCT system, a femtosecond surgical laser as a light source for the surgical laser beam can also be used as the light source for the OCT system.

Figure 15:
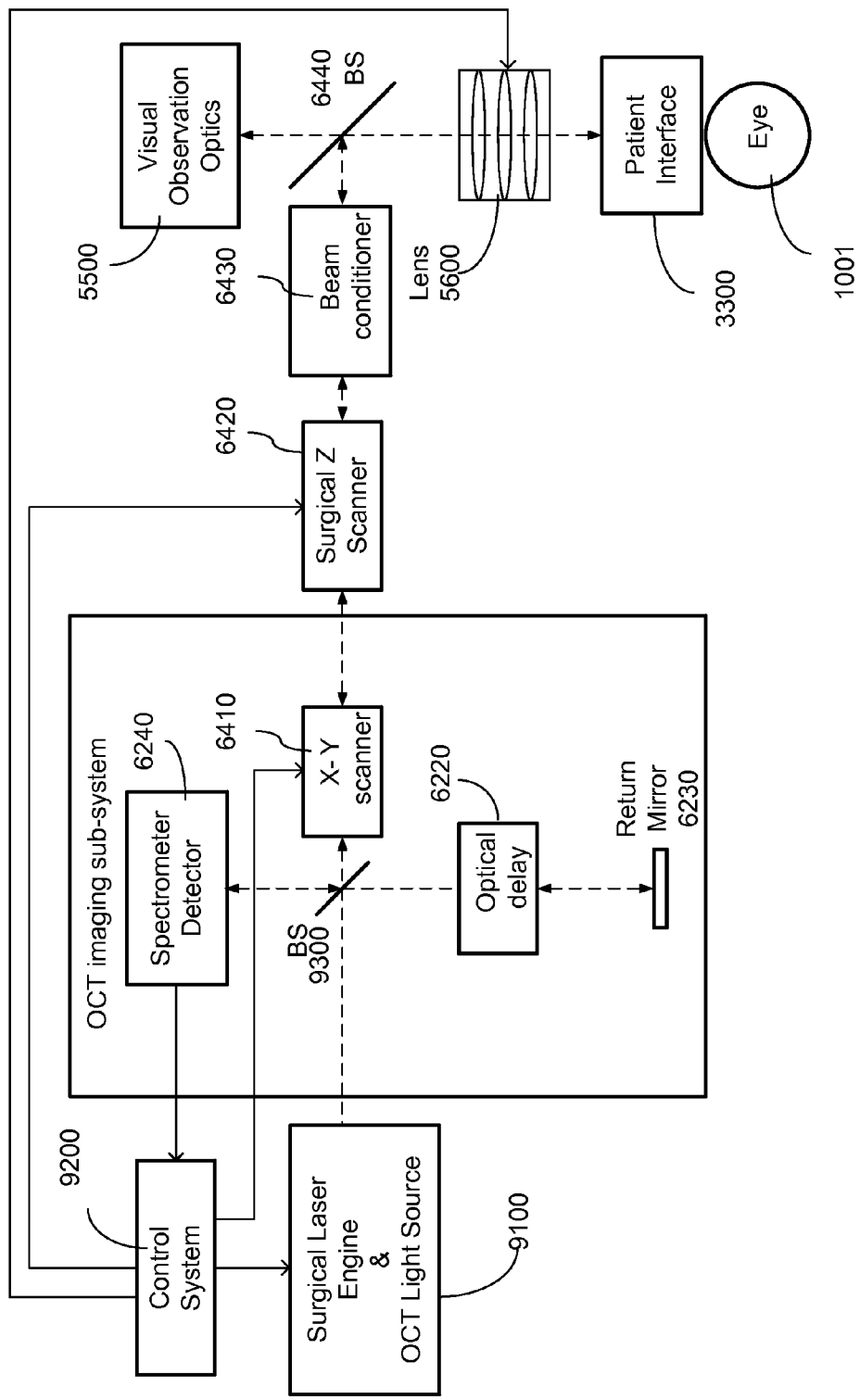

FIG. 15 shows an example where a femtosecond pulse laser in a light module 9100 is used to generate both the surgical laser beam for surgical operations and the probe light beam for OCT imaging. A beam splitter 9300 is provided to split the laser beam into a first beam as both the surgical laser beam and the signal beam for the OCT and a second beam as the reference beam for the OCT. The first beam is directed through an x-y scanner 6410 which scans the beam in the x and y directions perpendicular to the propagation direction of the first beam and a second scanner (z scanner) 6420 that changes the divergence of the beam to adjust the focusing of the first beam at the target tissue 1001. This first beam performs the surgical operations at the target tissue 1001 and a portion of this first beam is back scattered to the patient interface and is collected by the objective lens as the signal beam for the signal arm of the optical interferometer of the OCT system. This returned light is combined with the second beam that is reflected by a return mirror 6230 in the reference arm and is delayed by an adjustable optical delay element 6220 for a time-domain OCT to control the path difference between the signal and reference beams in imaging different depths of the target tissue 1001. The control system 9200 controls the system operations.

Surgical practice on the cornea has shown that a pulse duration of several hundred femtoseconds may be sufficient to achieve good surgical performance, while for OCT of a sufficient depth resolution broader spectral bandwidth generated by shorter pulses, e.g., below several tens of femtoseconds, are needed. In this context, the design of the OCT device dictates the duration of the pulses from the femtosecond surgical laser.

Figure 16:
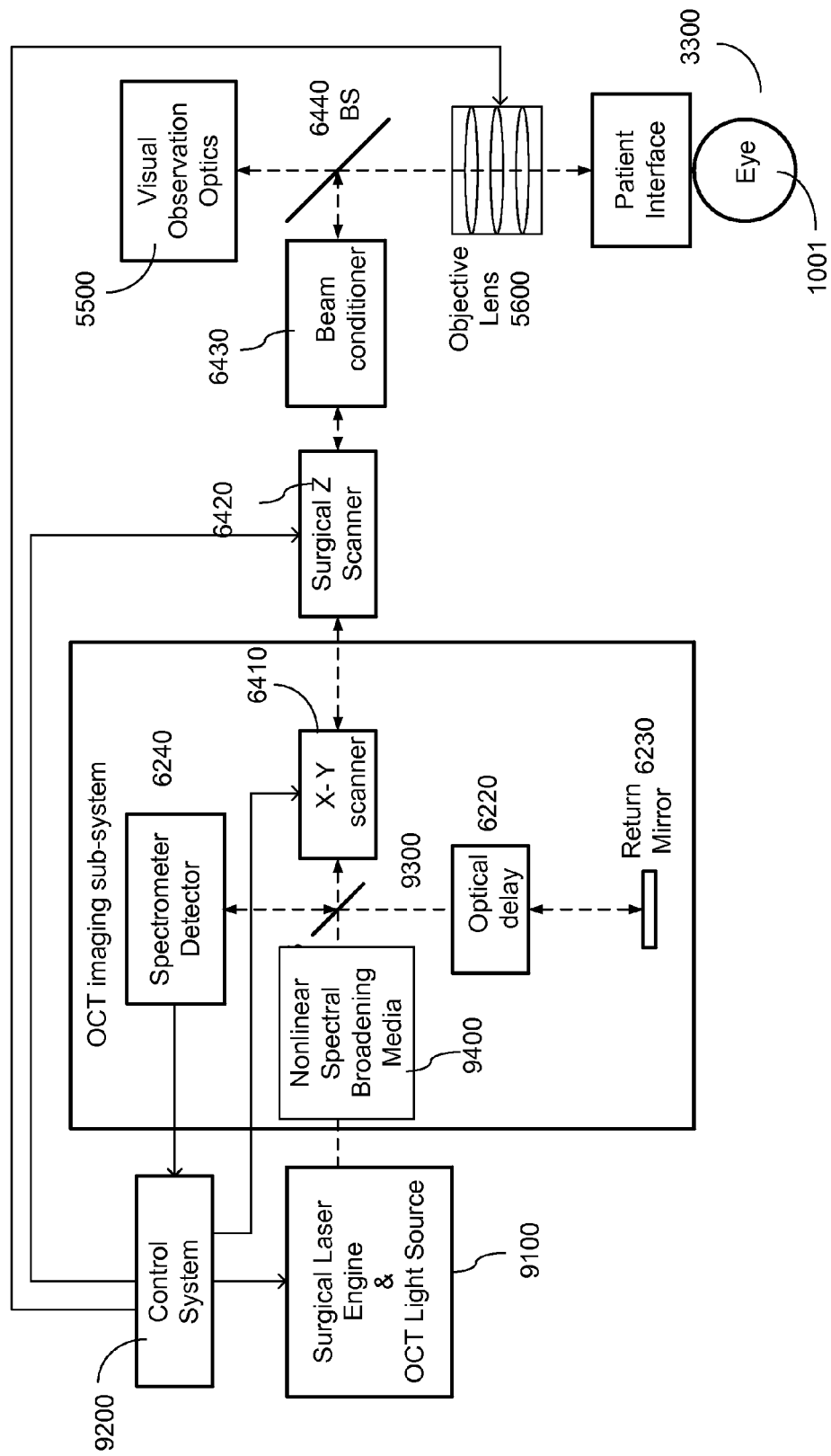

FIG. 16 shows another imaging-guided system that uses a single pulsed laser 9100 to produce the surgical light and the imaging light. A nonlinear spectral broadening media 9400 is placed in the output optical path of the femtosecond pulsed laser to use an optical non-linear process such as white light generation or spectral broadening to broaden the spectral bandwidth of the pulses from a laser source of relatively longer pulses, several hundred femtoseconds normally used in surgery. The media 9400 can be a fiber-optic material, for example. The light intensity requirements of the two systems are different and a mechanism to adjust beam intensities can be implemented to meet such requirements in the two systems. For example, beam steering minors, beam shutters or attenuators can be provided in the optical paths of the two systems to properly control the presence and intensity of the beam when taking an OCT image or performing surgery in order to protect the patient and sensitive instruments from excessive light intensity.

In operation, the above examples in FIGS. 8-16 can be used to perform imaging-guided laser surgery.

Figure 17:
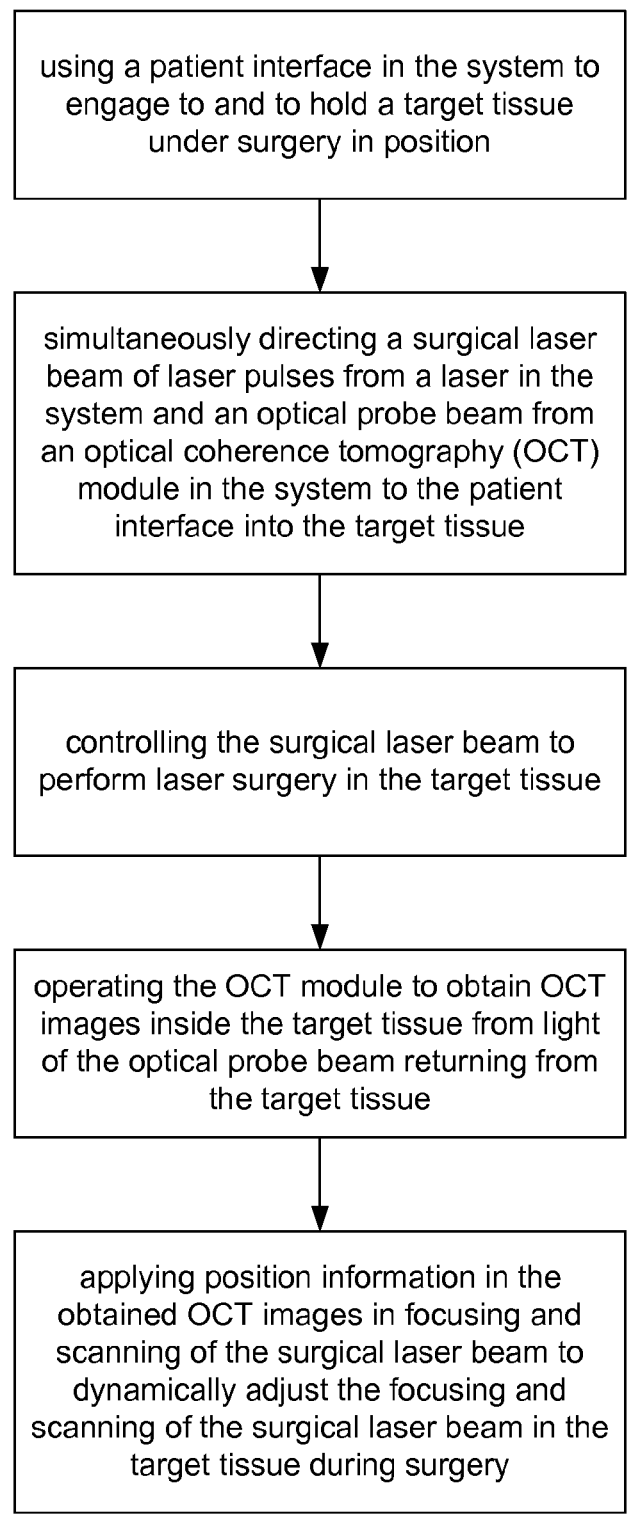
FIG. 17 shows an example of a method for performing laser surgery by suing an imaging-guided laser surgical system.

FIG. 17 shows one example of a method for performing laser surgery by using an imaging-guided laser surgical system. This method uses a patient interface in the system to engage to and to hold a target tissue under surgery in position and simultaneously directs a surgical laser beam of laser pulses from a laser in the system and an optical probe beam from the OCT module in the system to the patient interface into the target tissue. The surgical laser beam is controlled to perform laser surgery in the target tissue and the OCT module is operated to obtain OCT images inside the target tissue from light of the optical probe beam returning from the target tissue. The position information in the obtained OCT images is applied in focusing and scanning of the surgical laser beam to adjust the focusing and scanning of the surgical laser beam in the target tissue before or during surgery.

While this specification contains many specifics, these should not be construed as limitations on the scope of any invention or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The invention claimed is:

1. A method for guiding an eye surgery, comprising the steps of;
   creating first scan data by determining a depth of an eye target region at a first set of points along a first arc by one of an optical coherence tomographic (OCT) imaging system and an interference-based imaging system:
   creating second scan data by determining a depth of the eye target region at a second set of points along a second arc by the one of the OCT imaging system and the interference-based imaging system;
   determining target region parameters based on the first and second scan data by a computer controller;
   wherein the determining target region parameters step comprises:

fitting a sinusoidal function or Fourier harmonics with at least one fitting parameter to the first and second scan data; and determining the target region parameters using the fitting parameter; and assisting an adjusting of one or more surgical position parameters according to the determined target region parameters by the computer controller.

2. The method of claim 1, wherein:

the eye target region is one of a corneal target region, an anterior lens surface, a posterior lens surface, a lens target region, an ophthalmic layer, and a surface defined by a pupil.

3. The method of claim 1, wherein:

at least one of the first arc and the second arc forms at least part of a closed loop.

4. The method of claim 1, wherein:

the first arc is a portion of a first intersection line where a first scanning surface intersects the eye target region; and the second arc is a portion of a second intersection line where a second scanning surface intersects the eye target region.

5. The method of claim 1, wherein:

the first arc is a portion of a first intersection line where a first cylinder intersects the eye target region; and the second arc is a portion of a second intersection line where a second cylinder intersects the eye target region.

6. The method of claim 5, wherein:

the first cylinder and the second cylinder are concentric, sharing a Z axis.

7. The method of claim 5, wherein:

a Z axis of the second cylinder is offset from a Z axis of the first cylinder.

8. The method of claim 1, wherein the determining target region parameters step comprises:

extracting scan characteristics from the first and second scan data.

9. The method of claim 8, wherein the extracting scan characteristics step comprises:

extracting a first amplitude and a first phase of the first scan data; and extracting a second amplitude and a second phase of the second scan data.

10. The method of claim 9, wherein the determining of target region parameters step comprises:

determining a position parameter of a center of the target region based on the first amplitude, first phase, second amplitude and second phase.

11. The method of claim 9, wherein the determining of the target region parameters step comprises:

determining an object shape parameter of the target region based on the first amplitude, first phase, second amplitude and second phase.

12. The method of claim 9, wherein the determining of the target region parameters step comprises:

determining an object orientation parameter based on the first amplitude, first phase, second amplitude and second phase.

13. The method of claim 9, wherein the determining of the target region parameters step comprises:

determining a position parameter update, related to a position of the target region and a reference point.

14. The method of claim 1, wherein the adjusting the surgical position parameter comprises:

adjusting a position parameter of a surgical pattern center to align the surgical pattern center with a center of the target region.

15. The method of claim 1, wherein the method contains:

no more scans after the first scan and the second scan.

16. The method of claim 1, wherein:

the time from the starting of the first scanning step to the finishing of the determining the surgical position parameters step is no more than one of 100 milliseconds, 1,000 milliseconds and 10,000 milliseconds.

17. The method of claim 1, wherein:

at least one of the first and second arc is elliptical.

18. The method of claim 1, wherein:

at least one of the first arc and the second arc is an open arc; and at least one of the first scan data and the second scan data have a maximum and a minimum.

19. The method of claim 1, wherein the eye target region is a region of a lens of the eye;

the target region parameters comprise a shape parameter of the lens, a tilt parameter of the lens, and a position parameter of the lens.

20. The method of claim 1, wherein:

projections of the first arc and the second arc to a plane, transverse to an optical axis of the imaging system, are arcs.

* * * * *